US009658463B2

(12) United States Patent
Imamura et al.

(10) Patent No.: US 9,658,463 B2
(45) Date of Patent: May 23, 2017

(54) IMAGING DEVICE AND IMAGING SYSTEM

(71) Applicant: Panasonic Corporation, Osaka (JP)

(72) Inventors: Norihiro Imamura, Osaka (JP);
Tsuguhiro Korenaga, Osaka (JP);
Michihiro Yamagata, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 394 days.

(21) Appl. No.: 14/008,783

(22) PCT Filed: Feb. 1, 2013

(86) PCT No.: PCT/JP2013/000566
§ 371 (c)(1),
(2) Date: Sep. 30, 2013

(87) PCT Pub. No.: WO2013/114891
PCT Pub. Date: Aug. 8, 2013

(65) Prior Publication Data
US 2014/0055661 A1 Feb. 27, 2014

(30) Foreign Application Priority Data
Feb. 3, 2012 (JP) .................... 2012-021696

(51) Int. Cl.
*G02B 27/28* (2006.01)
*A61B 1/00* (2006.01)
(Continued)

(52) U.S. Cl.
CPC .......... *G02B 27/28* (2013.01); *A61B 1/00096* (2013.01); *A61B 1/041* (2013.01);
(Continued)

(58) Field of Classification Search
CPC ...... G02B 27/28; G02B 27/286; G02B 13/14; G02B 5/201; G02B 3/0056; G02B 5/3033;
(Continued)

(56) References Cited

U.S. PATENT DOCUMENTS 4,318,123 A 3/1982 Knop
5,076,687 A * 12/1991 Adelson .............. G01C 3/08
250/201.7
(Continued)

FOREIGN PATENT DOCUMENTS

CN 1261755 A 8/2000
CN 1860780 A 11/2006
(Continued)

OTHER PUBLICATIONS

International Search Report for corresponding International Application No. PCT/JP2013/000566 mailed May 7, 2013.
(Continued)

*Primary Examiner* — Ahmed A Berhan
(74) *Attorney, Agent, or Firm* — Renner, Otto, Boisselle & Sklar, LLP

(57) ABSTRACT

An imaging apparatus disclosed in the present application includes a lens optical system L, an imaging device N including a plurality of first and second pixels P1 and P2, and an arrayed optical device K, wherein: the lens optical system L includes a first optical region D1 which primarily passes therethrough light oscillating in a direction of a first polarization axis and a second optical region D2 which passes therethrough light oscillating in every direction; and the arrayed optical device K makes light having passed through the first optical region D1 incident on the first pixels P1 and makes light having passed through the second optical region D2 incident on the second pixels P2.

19 Claims, 25 Drawing Sheets

(51) Int. Cl.

| | |
|---|---|
| *G02B 13/14* | (2006.01) |
| *G01S 7/499* | (2006.01) |
| *G01S 17/89* | (2006.01) |
| *B60W 40/06* | (2012.01) |
| *G01N 21/47* | (2006.01) |
| *G02B 5/20* | (2006.01) |
| *G02B 5/30* | (2006.01) |
| *G02B 3/00* | (2006.01) |
| *A61B 5/00* | (2006.01) |
| *A61B 1/04* | (2006.01) |
| *G01N 21/21* | (2006.01) |
| *G01N 21/359* | (2014.01) |

(52) U.S. Cl.
CPC .......... *A61B 5/0077* (2013.01); *A61B 5/441* (2013.01); *B60W 40/06* (2013.01); *G01N 21/21* (2013.01); *G01N 21/4738* (2013.01); *G01S 7/499* (2013.01); *G01S 17/89* (2013.01); *G02B 3/0056* (2013.01); *G02B 5/201* (2013.01); *G02B 5/3033* (2013.01); *G02B 13/14* (2013.01); *G02B 27/286* (2013.01); *A61B 1/04* (2013.01); *G01N 21/359* (2013.01)

(58) Field of Classification Search
CPC .... G02B 5/3025; G02B 27/0961; G02B 5/30; A61B 1/00096; A61B 5/441; A61B 5/0077; A61B 1/041; G01S 7/499; G01S 17/89; G01N 21/4738; G01N 21/21; G01N 21/359; B60W 40/06; H04N 5/2256

See application file for complete search history.

(56) References Cited

U.S. PATENT DOCUMENTS

| | | | |
|---|---|---|---|
| 6,396,873 | B1 | 5/2002 | Goldstein et al. |
| 6,573,950 | B1 | 6/2003 | Hirata et al. |
| 2001/0017649 | A1 | 8/2001 | Yaron |
| 2001/0033326 | A1 | 10/2001 | Goldstein et al. |
| 2003/0197812 | A1 | 10/2003 | Hirata et al. |
| 2003/0202127 | A1 | 10/2003 | Hirata et al. |
| 2003/0231880 | A1 | 12/2003 | Irving et al. |
| 2005/0088576 | A1 | 4/2005 | Hirata et al. |
| 2008/0266655 | A1 | 10/2008 | Levoy et al. |
| 2009/0141361 | A1 | 6/2009 | Yamagata et al. |
| 2009/0315993 | A1 | 12/2009 | Hirai |
| 2011/0129165 | A1* | 6/2011 | Lim .................. H04N 5/23212 382/255 |
| 2011/0310280 | A1 | 12/2011 | Goto |
| 2011/0316983 | A1 | 12/2011 | Hiramoto et al. |
| 2012/0002018 | A1 | 1/2012 | Hiramoto et al. |
| 2012/0112037 | A1 | 5/2012 | Hiramoto et al. |
| 2012/0212587 | A1* | 8/2012 | Otani ................. H04N 13/021 348/49 |
| 2012/0268602 | A1 | 10/2012 | Hirai et al. |
| 2013/0063569 | A1 | 3/2013 | Sato et al. |
| 2013/0070140 | A1* | 3/2013 | Gove ................... G02B 3/0056 348/302 |

FOREIGN PATENT DOCUMENTS

| | | |
|---|---|---|
| JP | 10-048535 A | 2/1998 |
| JP | 2000-214527 A | 8/2000 |
| JP | 2003-523646 T | 8/2003 |
| JP | 2004-046162 A | 2/2004 |
| JP | 2008-237243 A | 10/2008 |
| JP | 2009-139356 A | 6/2009 |
| JP | 2010-025915 A | 2/2010 |
| JP | 2011-097987 A | 5/2011 |
| JP | 2011-150686 A | 8/2011 |
| JP | 2012-003080 A | 1/2012 |
| WO | WO 2011/148851 A1 | 12/2011 |

OTHER PUBLICATIONS

Form PCT/ISA/237 for corresponding International Application No. PCT/JP2013/000566 dated May 7, 2013 and partial English translation.

Chinese Office Action and Search Report dated Jan. 29, 2016 for corresponding Chinese Application No. 201380000962.0 and English translation of Search Report.

* cited by examiner (a)     (b)

*FIG.19*
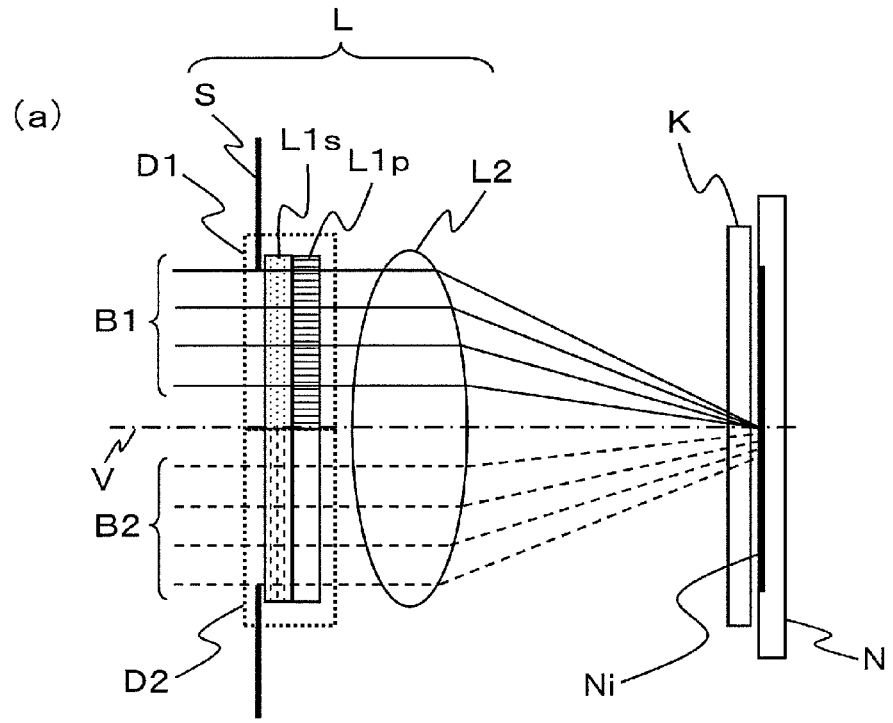
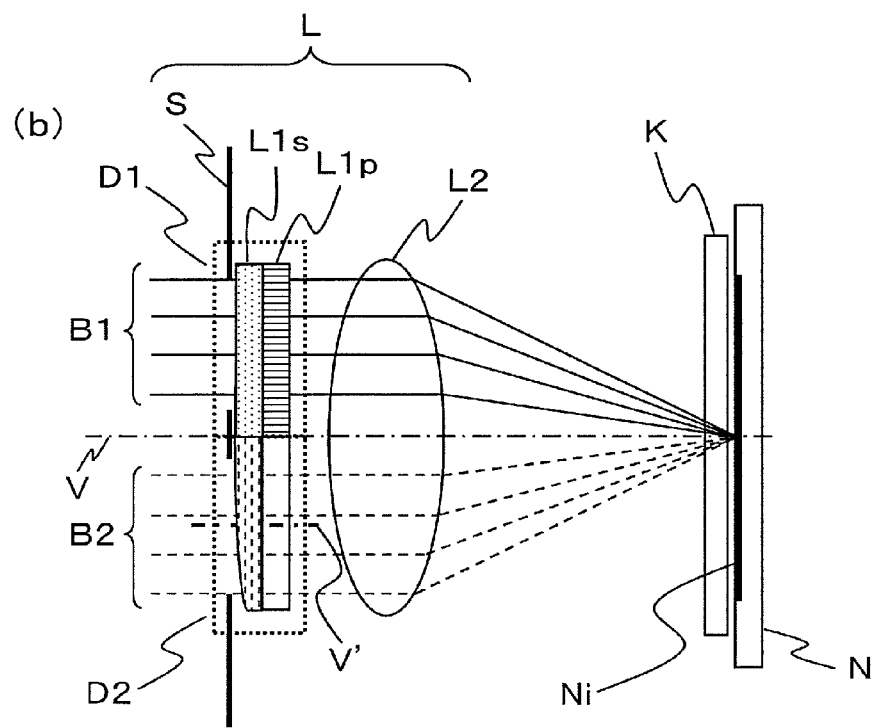

FIG.20
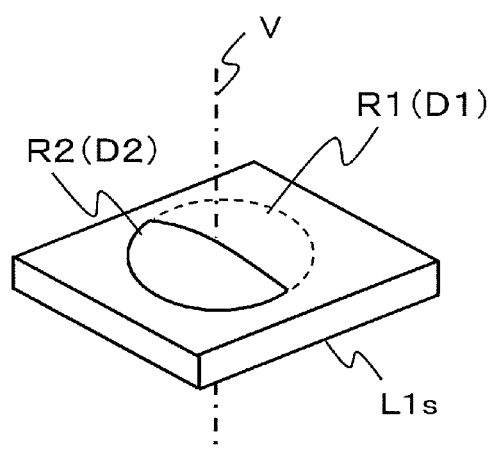
(a)
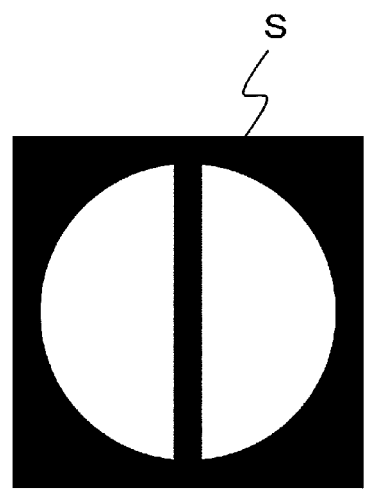
(b)
FIG.21
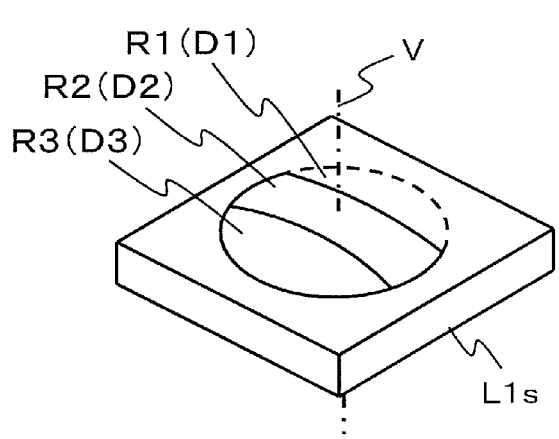
(a)
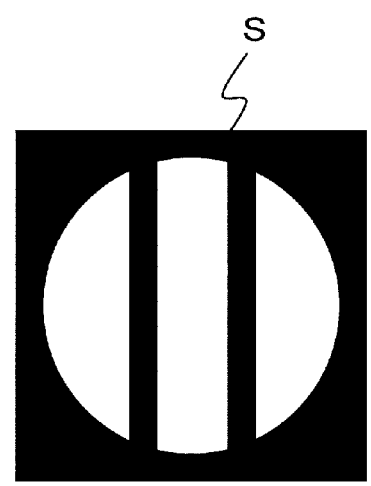
(b)

(a)   (b)

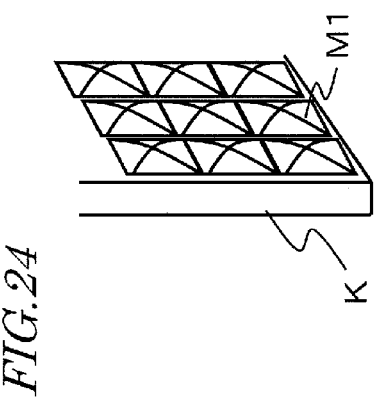
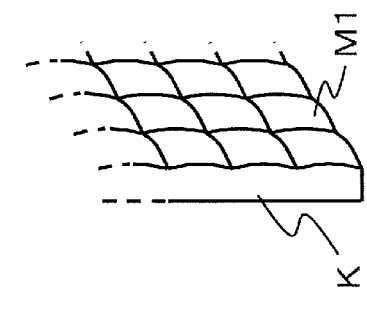
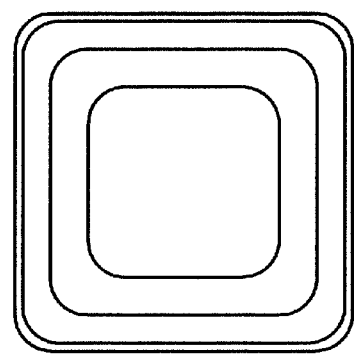
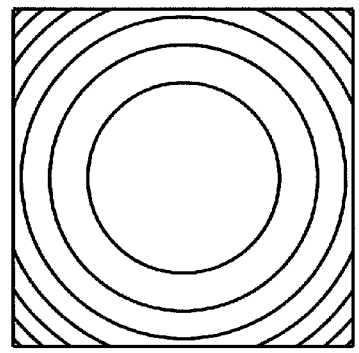
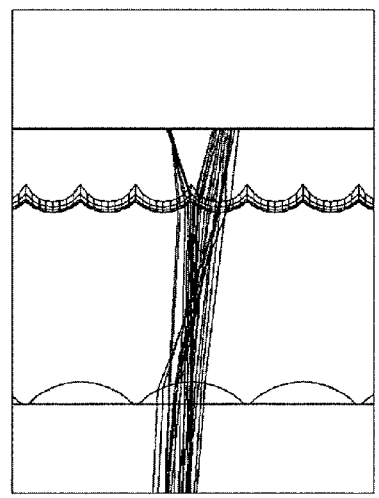
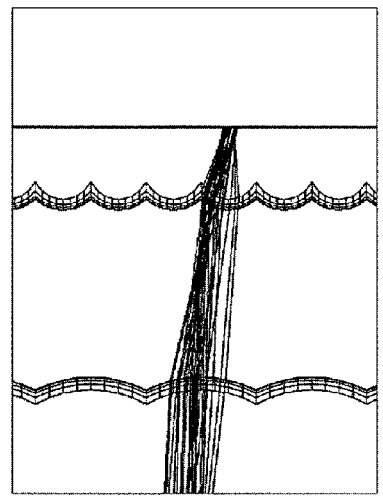
FIG. 24

FIG.29
(a) 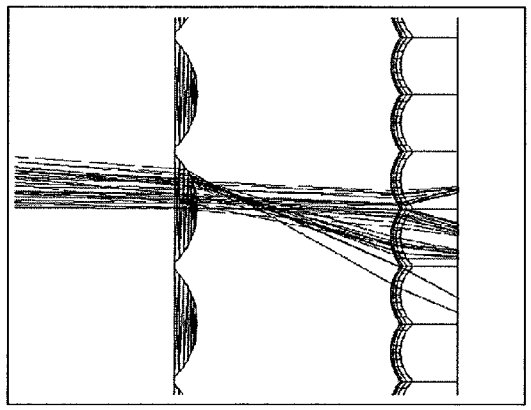
(b) 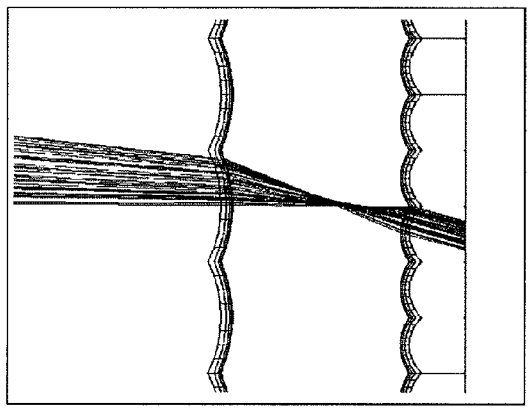
(c) 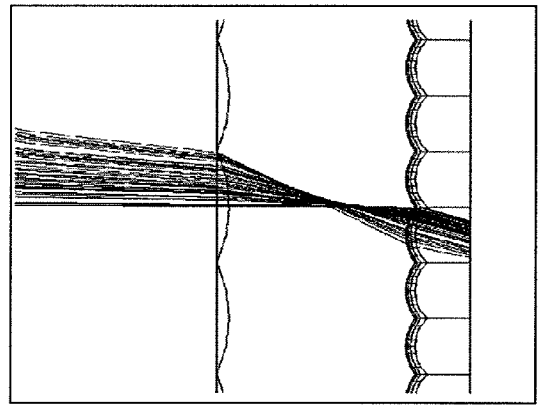

FIG.30
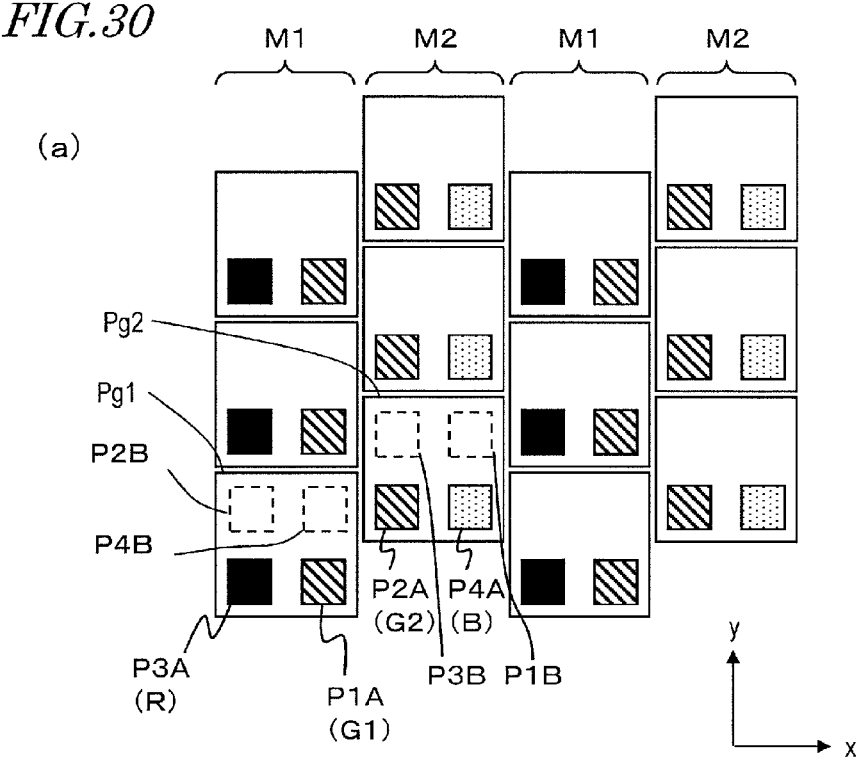
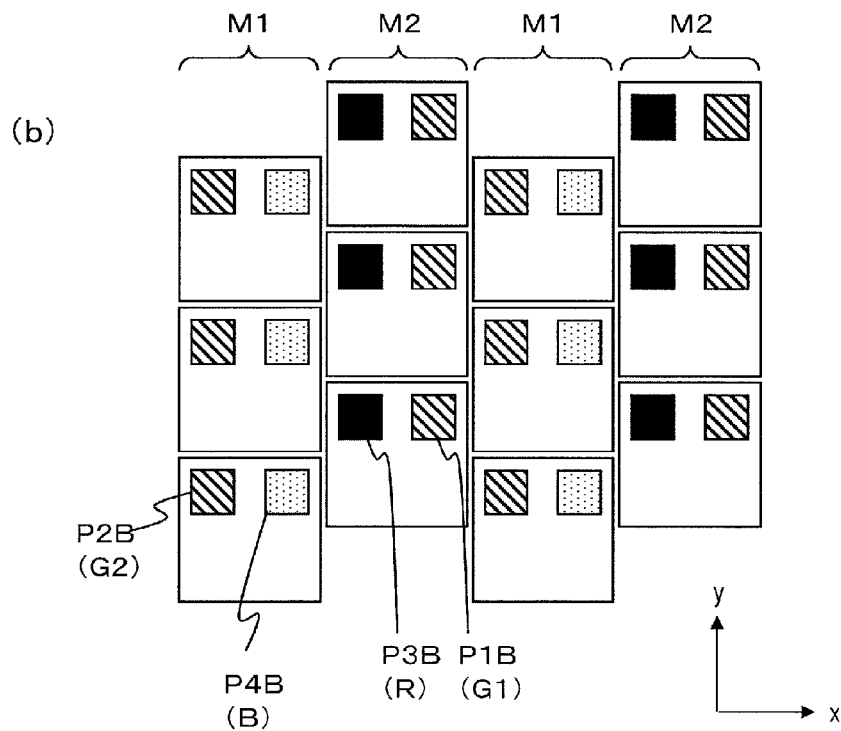

(a)    (b)

(a)    (b)

FIG.33
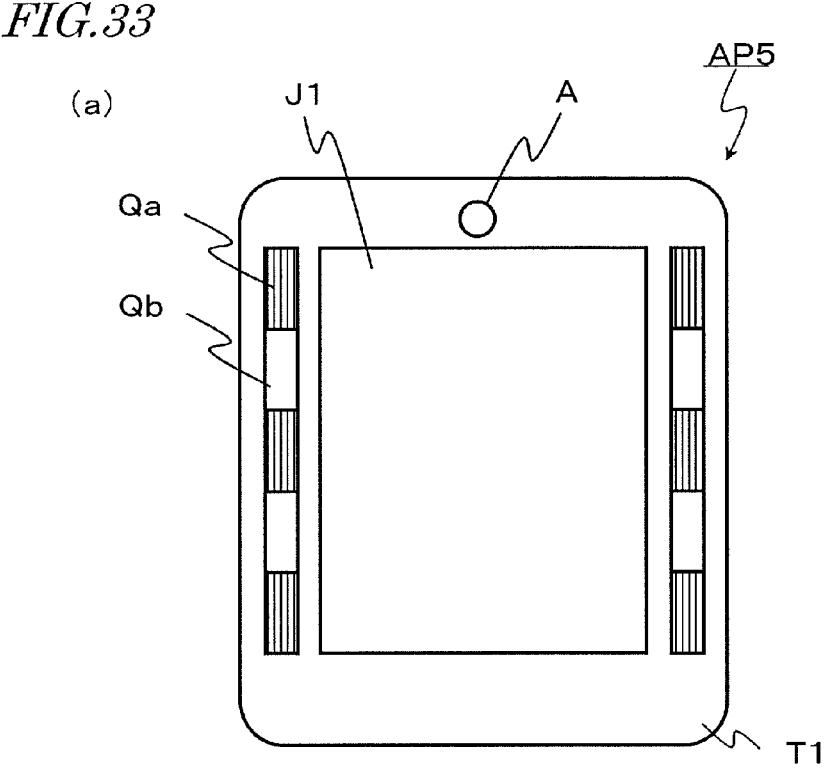
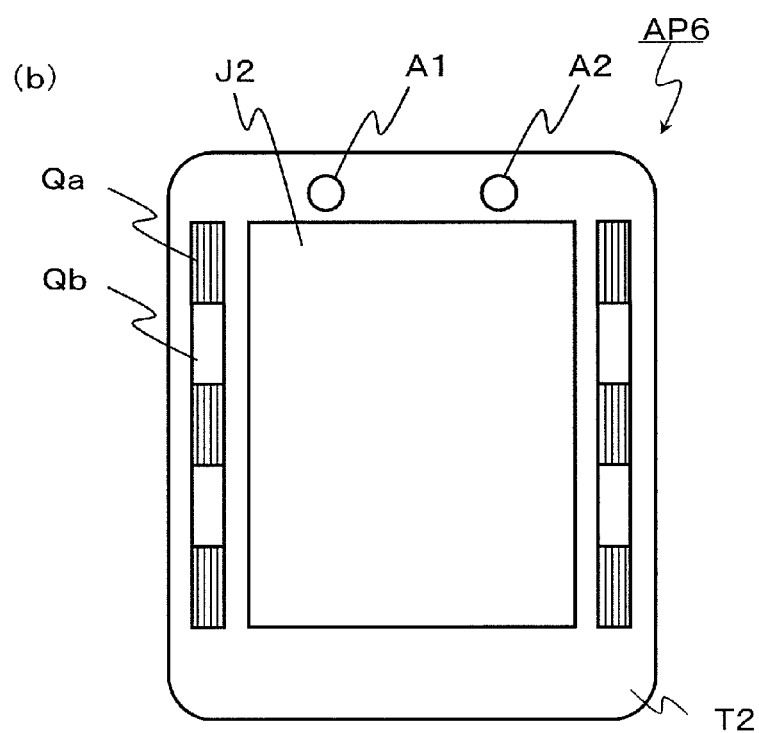

FIG.35
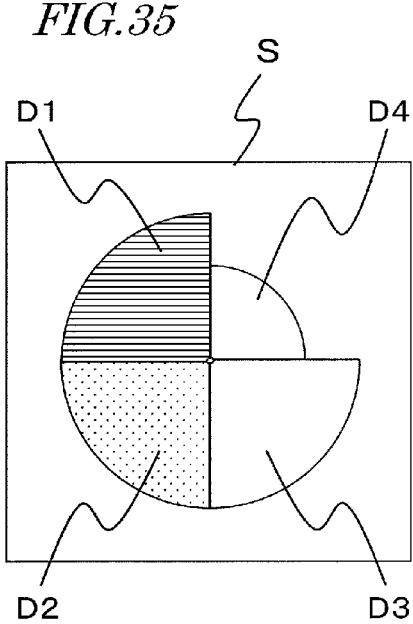
(a)
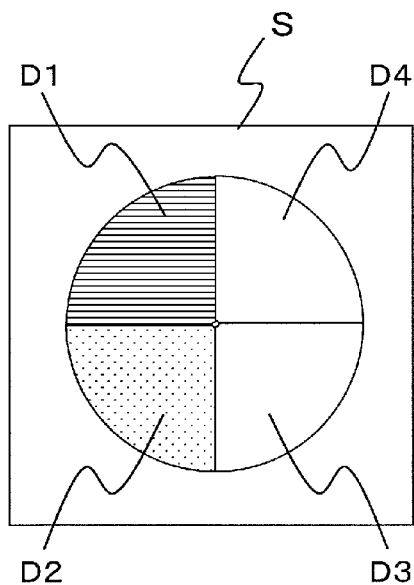
(b)
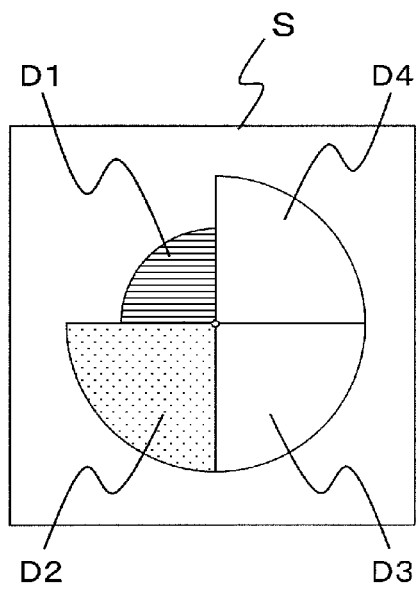
(c)
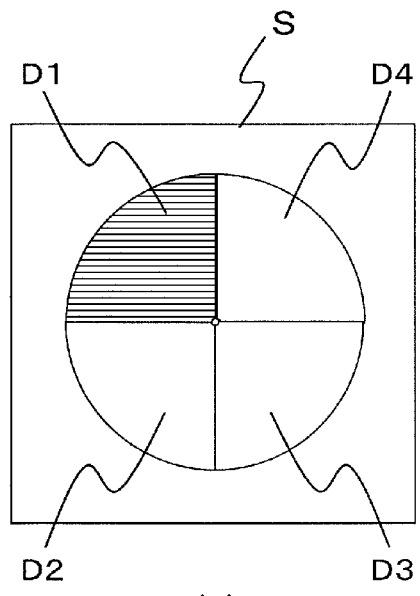
(d)

IMAGING DEVICE AND IMAGING SYSTEM

TECHNICAL FIELD

The present application relates to an imaging apparatus, such as a camera, and an imaging system.

BACKGROUND ART

In the field of vehicle cameras, an imaging apparatus has been disclosed, in which polarizers are provided in an optical path of a compound eye camera with a different polarization axis for each ommatidium, for detecting a road surface condition or a lane (Patent Document No. 1).

With cameras in the medical/beauty field, such as endoscopic systems and skin diagnosis systems, imaging apparatuses have been commercialized, which obtain both a non-polarized light image and a polarized light image.

These imaging apparatuses include a polarized illumination for irradiating a biological tissue with non-polarized light and light oscillating in the direction of a predetermined polarization axis. When a biological tissue is irradiated with light of a predetermined polarized component, reflected light off the biological surface is specular reflection light of which the polarized component is maintained, whereas reflected light off a living body deep part is scattered reflection light of which the polarized component is disturbed. Therefore, it is possible to obtain an image of the biological surface and an image of the living body deep part by arranging, on the side of the imaging apparatus, a polarization filter that passes therethrough light oscillating in a direction parallel to the polarization axis of the polarized illumination and a polarization filter that passes therethrough light oscillating in a direction perpendicular to the polarization axis of the illumination.

Such imaging apparatuses for obtaining images of different polarization characteristics have been disclosed in the art (Patent Document Nos. 2 and 3).

CITATION LIST

Patent Literature

Patent Document No. 1: Japanese Laid-Open Patent Publication No. 2010-25915
Patent Document No. 2: Japanese Laid-Open Patent Publication No. 2008-237243
Patent Document No. 3: Japanese Laid-Open Patent Publication No. 2011-97987

SUMMARY OF INVENTION

Technical Problem

However, with the above-described conventional techniques, there has been a demand for an imaging apparatus capable of capturing a movie with a simpler configuration.

A non-limiting example embodiment of the present application provides an imaging apparatus capable of capturing a movie with a simpler configuration.

Solution to Problem

An imaging apparatus according to one aspect of the present invention includes: a lens optical system; an imaging device including at least a plurality of first pixels and a plurality of second pixels on which light having passed through the lens optical system is incident; and an arrayed optical device being arranged between the lens optical system and the imaging device and including a plurality of optical elements each having a lens surface, wherein: the lens optical system includes a plurality of optical regions, and the plurality of optical regions include at least a first optical region which primarily passes therethrough light oscillating in a direction of a first polarization axis and a second optical region which passes therethrough light oscillating in any direction; and the plurality of optical elements of the arrayed optical device make light having passed through the first optical region incident on the plurality of first pixels and light passing through the second optical region incident on the plurality of second pixels.

Advantageous Effects of Invention

With the imaging apparatus according to one aspect of the present invention, it is possible to simultaneously obtain both a polarized light image and a non-polarized light image using a single imaging system. Where a motion video is recorded using the imaging apparatus of the present invention, no image shift will occur between a plurality of images even if the position of the object changes over time.

BRIEF DESCRIPTION OF DRAWINGS

FIGS. 19(a) and (b) are schematic diagrams showing an optical system and an imaging section according to Embodiment 8 of the present invention.

FIG. 20(a) is a perspective view showing the optical device L1s according to Embodiment 8 of the present invention, and FIG. 20(b) is a front view showing the stop S as seen from the object side.

FIG. 21(a) is a perspective view showing the optical device L1s according to another embodiment of Embodiment 8 of the present invention, and FIG. 21(b) is a front view showing the stop S as seen from the object side.

FIGS. 24(a1) and 24(b1) are perspective views of the arrayed optical device K according to Embodiment 9 of the present invention, FIGS. 24(a2) and 24(b2) are diagrams showing contour lines of optical devices, and FIGS. 24(a3) and 24(b3) are diagrams showing the results of light beam tracking simulations.

FIG. 28(a2) is a perspective view of the microlens array shown in FIG. 28(a1). FIG. 28(b1) is a diagram showing an arrangement of a microlens array having a rotationally symmetric shape with respect to the optical axis and the contour lines thereof. FIG. 28(b2) is a perspective view of the microlens array shown in FIG. 28(b1). FIG. 28(c1) is a diagram showing an arrangement in which cylindrical microlenses are shifted from one another by half the pitch and the contour lines thereof. FIG. 28(c2) is a perspective view of the cylindrical microlens array shown in FIG. 28(c1).

FIG. 29(a) is a diagram showing the results of a light beam tracking simulation in a case where the microlens shown in FIGS. 28(a1) and 28(a2) is applied to the arrayed optical device of Embodiment 12. FIG. 29(b) is a diagram showing the results of a light beam tracking simulation in a case where the microlens shown in FIGS. 28(b1) and 28(b2) is applied to the arrayed optical device of Embodiment 12. FIG. 29(c) is a diagram showing the results of a light beam tracking simulation in a case where the microlens shown in FIGS. 28(c1) and 28(c2) is applied to the arrayed optical device of Embodiment 12.

FIGS. 30(a) and (b) are diagrams obtained by extracting pixels at which light beams having passed through the first and second regions, respectively, arrive.

FIG. 33(a) is a front view showing an electronic mirror AP5 according to Embodiment 15, and FIG. 33(b) is a front view showing a stereoscopic electronic mirror AP6.

FIGS. 35(a), 35(b), 35(c) and 35(d) are front views showing an optical device and a stop in other embodiments of the present invention.

DESCRIPTION OF EMBODIMENTS

Figure 1:
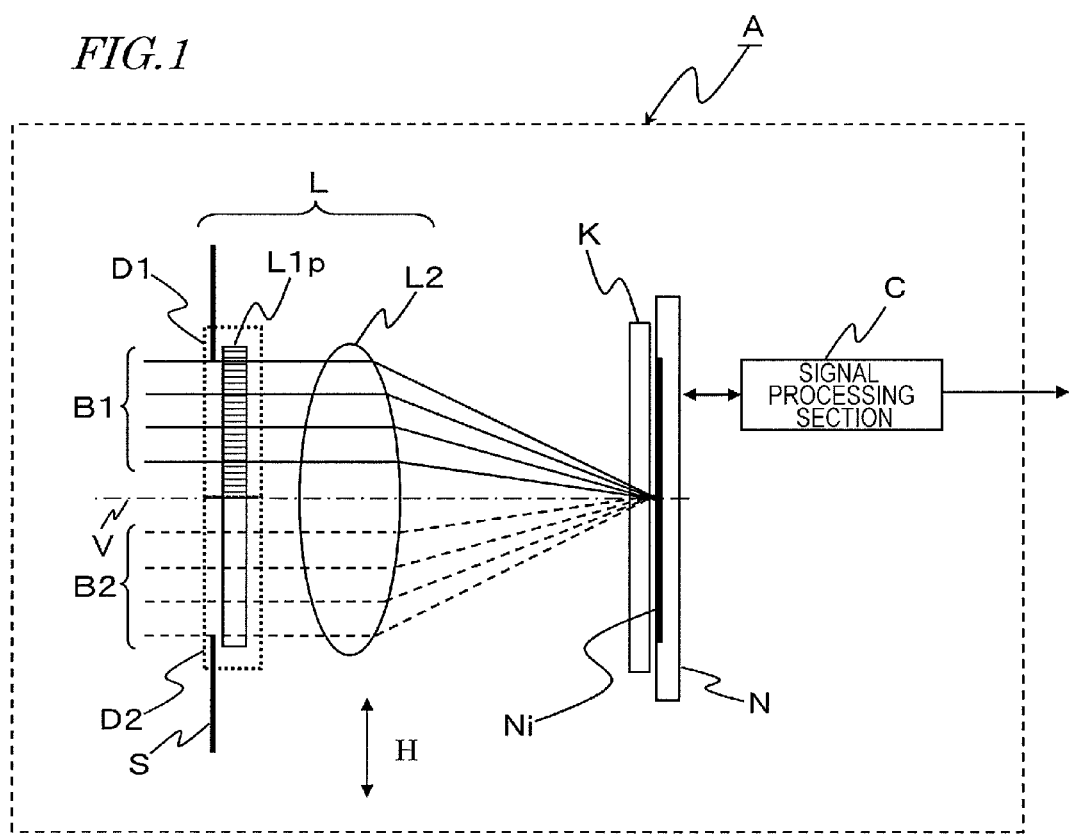
FIG. 1 is a schematic diagram showing Embodiment 1 of an imaging apparatus A according to the present invention.

The present inventors made an in-depth study on imaging apparatuses disclosed in Patent Document Nos. 1 to 3. With the apparatus disclosed in Patent Document No. 1, since the configuration is a compound eye configuration, the parallax between obtained images varies significantly depending on the object distance in applications where the focal length is long or the object distance is short. Therefore, detecting the condition by comparing the same object positions will require a separate signal process for extracting and correcting the parallax for each minute area of the image, thereby increasing the arithmetic operation. While a lens array is formed in front of the imaging device in the case of a compound eye, this arrangement requires that the effective diameter of a signal optical system be less than half the size of the image pickup area, thereby decreasing the degree of freedom in the optical design, thus making it difficult to realize an optical system capable of obtaining a sufficient resolution for the purpose of obtaining images. It is also difficult to realize an ultra-wide-angle optical system such as a fish-eye lens.

Patent Document No. 2 discloses a configuration for obtaining polarized light images of a plurality of wavelength bands by means of a plurality of polarized illuminations of different wavelength bands and a camera provided with a polarization filter which passes therethrough polarized components orthogonal to the polarized illumination. However, an image that can be captured with such a configuration is only an image including polarization information of only one kind of a polarization axis direction, and it is also not suitable for recording a motion video because images of different wavelength bands need to be captured in a time-division manner.

Patent Document No. 3 discloses a configuration for obtaining images of different polarized components by means of a polarization beam splitter. Such a configuration, however, requires a polarization beam splitter and a plurality of imaging devices, thereby increasing the size and the cost.

In view of such problems, the present inventors arrived at a novel imaging apparatus capable of obtaining both an image having polarization information and a normal image using a single image pickup optical system. One aspect of the present invention will be outlined below.

An imaging apparatus according to one aspect of the present invention includes: a lens optical system; an imaging device including at least a plurality of first pixels and a plurality of second pixels on which light having passed through the lens optical system is incident; and an arrayed optical device being arranged between the lens optical system and the imaging device and including a plurality of optical elements each having a lens surface, wherein: the lens optical system includes a plurality of optical regions, and the plurality of optical regions include at least a first optical region which primarily passes therethrough light oscillating in a direction of a first polarization axis and a second optical region which passes therethrough light oscillating in any direction; and the plurality of optical elements of the arrayed optical device make light having passed through the first optical region incident on the plurality of first pixels and light passing through the second optical region incident on the plurality of second pixels.

The first optical region may pass therethrough light of a first wavelength band, and the second optical region may pass therethrough light of a second wavelength band.

The first wavelength band may be a wavelength band of near-ultraviolet light.

The first wavelength band may include a predetermined band in a wavelength band from 400 nm to 600 nm.

The first wavelength band may be a wavelength band of near-infrared light.

The plurality of optical regions of the lens optical system may further include a third optical region other than the first and second optical regions; the third optical region may primarily pass therethrough light oscillating in a direction of a second polarization axis which is different from the first polarization axis; and the arrayed optical device may make light having passed through the third optical region incident on a plurality of third pixels other than the plurality of first and second pixels.

The plurality of optical regions of the lens optical system may further include third and fourth optical regions other than the first and second optical regions; the first, second, third and fourth optical regions may pass therethrough light of first, second, third and fourth wavelength bands which are different from one another; and the arrayed optical device may make light having passed through the third and fourth optical regions incident on a plurality of third and fourth pixels other than the plurality of first and second pixels.

The plurality of optical regions of the lens optical system may further include third and fourth optical regions other than the first and second optical regions; the first and third optical regions may pass therethrough light of the same wavelength band, and second and fourth optical regions may pass therethrough light of wavelength bands different from wavelength bands of light passing through the first and the third optical regions, respectively; and the arrayed optical device may make light having passed through the third and fourth optical regions incident on a plurality of third and fourth pixels, respectively, other than the plurality of first and second pixels.

The third optical region may primarily pass therethrough light oscillating in a direction of a second polarization axis different from the first polarization axis.

The imaging device may further include a plurality of third and fourth pixels on which light having passed through the lens optical system is incident; the plurality of optical regions may further include third and fourth optical regions; the third optical region may pass therethrough light oscillating in any direction; the arrayed optical device may make light having passed through the third and fourth optical regions incident on the plurality of third and fourth pixels; and the plurality of first, second and third pixels may include filters having first, second and third spectral transmittance characteristics, respectively.

The plurality of fourth pixels may have the first spectral transmittance characteristics; and the fourth optical region may pass therethrough light of a predetermined wavelength band and pass therethrough light oscillating in a direction of a second polarization axis different from the first polarization axis.

The first, second, third and fourth pixels of the imaging device may be arranged in a Bayer array.

An imaging apparatus according to another aspect of the present invention includes: a lens optical system including a filter which passes therethrough light of a predetermined band, and having a first region which primarily passes therethrough light oscillating in a direction of a first polarization axis, and a second region which is located at a position different from the first region and which passes therethrough light oscillating in any direction; an imaging device including a plurality of first pixels on which light having passed through the lens optical system is incident, a plurality of second pixels including a filter having first spectral transmittance characteristics, a plurality of third pixels including a filter having second spectral transmittance characteristics, and a plurality of fourth pixels including a filter having third spectral transmittance characteristics; and an arrayed optical device being arranged between the lens optical system and the imaging device and including a plurality of optical elements each having a lens surface, wherein the arrayed optical device makes light having passed through the first optical region incident on the plurality of first pixels, and makes light having passed through the second optical region incident on the plurality of second, third and fourth pixels.

An imaging apparatus according to another aspect of the present invention includes: a lens optical system includes a first region which primarily passes therethrough light oscillating in a direction of a first polarization axis, and a second region which is located at a position different from the first region and which passes therethrough light oscillating in any direction; an imaging device including a plurality of pixels and an imaging surface, wherein the plurality of pixels include a plurality of first and second pixels on which light having passed through the lens optical system is incident and which includes a filter having first spectral transmittance characteristics, a plurality of third pixels including a filter having second spectral transmittance characteristics, and a plurality of fourth pixels including a filter having third spectral transmittance characteristics; and an arrayed optical device being arranged between the lens optical system and the imaging device and including a plurality of optical elements each having a lens surface, wherein: the plurality of pixels are arranged on the imaging surface by being arranged in m rows in a second direction from a $1^{st}$ row to an $m^{th}$ (m is an integer greater than or equal to 2), each row being a group of pixels including 1 to l pixels arranged in a first direction (l is an integer greater than or equal to 2); a position of a center in the first direction of each of l pixels arranged in a $j^{th}$ row ($1 \leq j < m$) of the m rows is generally equal to a position of a center in the first direction of each of l pixels arranged in a $j+1^{th}$ row; and the plurality of optical elements are arranged on a surface of the arrayed optical device in t columns in the first direction from a $1^{st}$ column to a $t^{th}$ columns (t is an integer greater than or equal to 2), each column being a group of optical elements including 1 to s optical elements (s is an integer greater than or equal to 2) arranged in the second direction, wherein a position of a center in the second direction of an optical element arranged in a $k^{th}$ column ($1 \leq k < t$) of the t columns is shifted in the second direction from a position of a center in the second direction of an optical element arranged in a $k+1^{th}$ column.

The plurality of first pixels may include 1A and 1B pixels, the plurality of second pixels may include 2A and 2B pixels, the plurality of third pixels may include 3A and 3B pixels, and the plurality of fourth pixels may include 4A and 4B pixels; an optical element in the $k^{th}$ row may make light having passed through the first region incident on the 1A pixel and the 3A pixel and make light having passed through the second region incident on the 2B pixel and the 4B pixel; and an optical element in the $k+1^{th}$ row may make light having passed through the first region incident on a plurality of 2A pixels and the 4A pixel and make light having passed through the second region incident on the 1B pixel and the 3B pixel.

At least two or more of the plurality of optical regions may have different levels of optical power from each other; and focus positions of light having passed through the plurality of optical regions may be closer to each other as compared with a case where the plurality of optical regions have an equal optical power.

The imaging apparatus may further include a light-blocking region at a position corresponding to a boundary portion between the first region and the second region.

The lens optical system may be an image-side telecentric optical system.

The lens optical system may be an image-side non-telecentric optical system; and an arrangement of the arrayed optical device may be offset with respect to an arrangement of pixels of the imaging device outside an optical axis of the lens optical system.

The arrayed optical device may be a lenticular lens.

In the arrayed optical device, the lens surfaces of the plurality of optical elements may each be a cylindrical surface extending in a first direction, and the plurality of optical elements may be arranged in a second direction; and each of the plurality of optical elements may be arranged so as to correspond to two rows of pixels including one row of first pixels and one row of second pixels.

The arrayed optical device may be a microlens array.

In the arrayed optical device, the lens surfaces of the plurality of optical elements may each have a rotationally symmetric shape.

Each of the plurality of optical elements may be arranged so as to correspond to one of the plurality of first pixels, one of the plurality of second pixels, one of the plurality of third pixels, and one of the plurality of fourth pixels.

The arrayed optical device may be formed on the imaging device.

The imaging apparatus may further include a microlens provided between the arrayed optical device and the imaging device, wherein the arrayed optical device is formed on the imaging device with the microlens interposed therebetween.

The microlens provided between the arrayed optical device and the imaging device may be a binary diffraction optical device or a multi-level diffraction optical device.

The lens optical system may further include a stop; and the plurality of optical regions may be arranged in the vicinity of the stop.

The imaging apparatus may further include a signal processing section for generating an image based on a signal obtained by the imaging device.

An imaging system according to one aspect of the present invention includes any of the imaging apparatuses set forth above; and a signal processing section for generating an image based on a signal obtained by the imaging apparatus.

An imaging system according to one aspect of the present invention includes any of the imaging apparatuses set forth above; and a polarized illumination.

The imaging system may further include a non-polarized illumination.

An imaging system according to another aspect of the present invention includes: at least one of the imaging apparatuses set forth above; a polarized illumination; and a display device for displaying an image obtained by the imaging apparatus.

The at least one imaging apparatus may be two imaging apparatuses; and the display device may display two images obtained by the two imaging apparatuses.

The display device may be a liquid crystal display including a polarization filter on an object side; and a direction of a polarization axis of the polarization filter in the liquid crystal display may be equal to a direction of a polarization axis of the polarized illumination.

Embodiments of the imaging apparatus according to the present invention will now be described with reference to the drawings.

Embodiment 1

FIG. 1 is a schematic diagram showing an imaging apparatus A of Embodiment 1. The imaging apparatus A of the present embodiment includes a lens optical system L whose optical axis is V, an arrayed optical device K arranged in the vicinity of the focal point of the lens optical system L, a monochromatic imaging device N, and a signal processing section C.

The lens optical system L includes a stop S receiving light from an object (not shown), an optical device L1p receiving light having passed through the stop S, and a lens L2 receiving light having passed through the optical device L1p. The lens optical system L includes first and second optical regions D1 and D2.

The lens L2 may be formed by a single lens or formed by a plurality of lenses. It may also be divided into a plurality of lenses arranged on both sides of the stop S. FIG. 1 shows a single-lens configuration.

The optical device L1p is arranged in the vicinity of the stop S, and is formed by a portion located in the first optical region D1 and a portion located in the second optical region D2. Arranged in the first optical region D1 is a polarization filter that passes therethrough light oscillating in the direction of the first polarization axis (transmission axis), and arranged in the second optical region D2 is a glass plate that passes therethrough light oscillating in every direction. For example, where there is a deviation in oscillation direction of light from the object, light passing through the first optical region D1 may be attenuated significantly depending on the oscillation direction, but there is little attenuation through the second optical region D2 because light oscillating in every direction (light oscillating in any direction) passes therethrough.

In the present embodiment, light beams having passed through the two optical regions D1 and D2 pass through the lens L2 and are then incident on the arrayed optical device K. The arrayed optical device K makes light beams having passed through the optical region D1 incident on a plurality of pixels P1 of the imaging device N and light beams having passed through the optical region D2 incident on a plurality of pixels P2 of the imaging device N. The signal processing section C generates and outputs image information corresponding to a light beam oscillating in the direction of the first polarization axis from brightness values obtained from pixels P1, and generates and outputs image information corresponding to a light beam oscillating in every direction including the first polarization axis from brightness values obtained from pixels P2.

Figure 4:
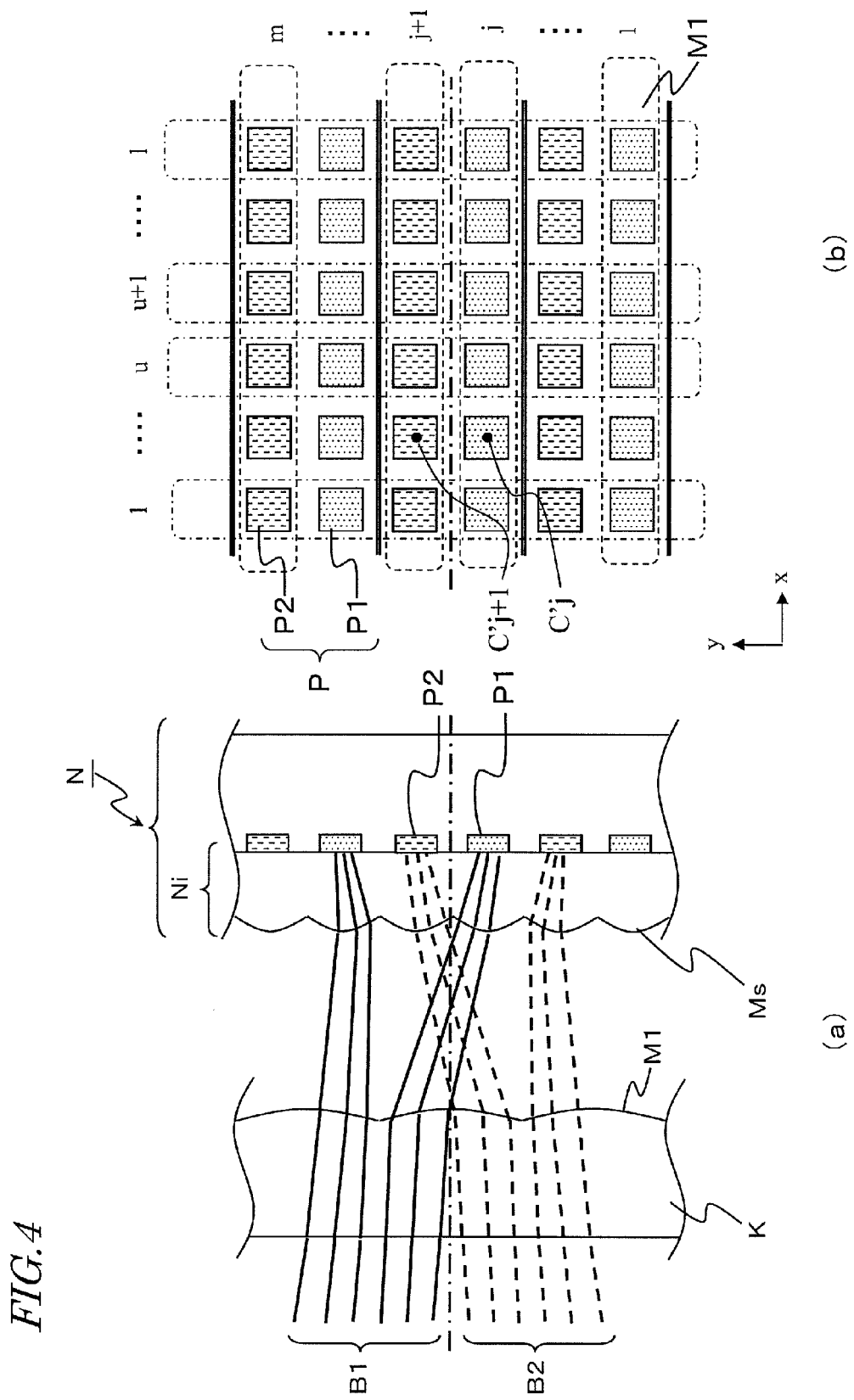
FIG. 4($a$) is an enlarged view of the arrayed optical device K and an imaging device N shown in FIG. 1 according to Embodiment 1, and FIG. 4($b$) is a diagram showing the positional relationship between the arrayed optical device K and pixels on the imaging device N.

In FIG. 1, light beams B1 are light beams passing through the first optical region D1 on the optical device L1p, and light beams B2 are light beams passing through the second optical region D2 on the optical device L1p. The light beams B1 and B2 pass through the stop S, the optical device L1p, the lens L2 and the arrayed optical device K in this order to arrive at an imaging surface Ni (shown in FIG. 4) on the imaging device N.

Figure 2:
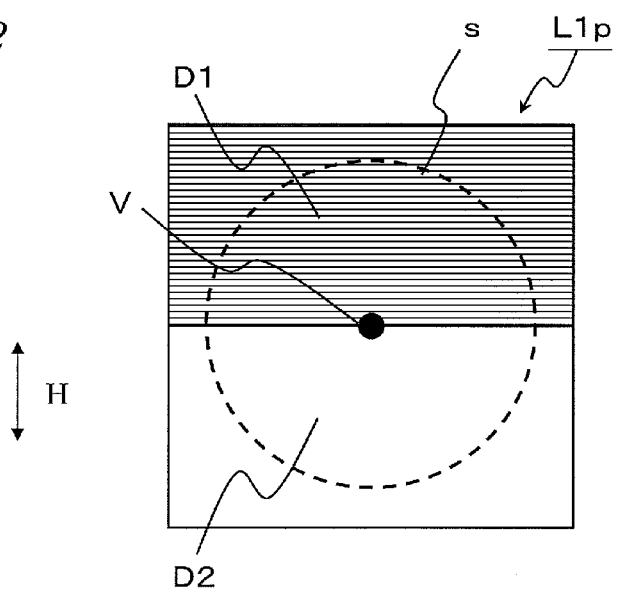
FIG. 2 is a front view showing first and second optical regions D1 and D2 of an optical device L1$p$ according to Embodiment 1 of the present invention, as seen from the object side.

FIG. 2 is a front view showing the first and second optical regions D1 and D2 as seen from the object side. The first and second optical regions D1 and D2 of the optical device L1p are formed by two-fold division in the up-down direction in a plane vertical to the optical axis V with the optical axis V being the center of the boundary. In FIG. 2, the broken line s represents the opening area of the stop S. An arrow H in FIGS. 1 and 2 denotes the horizontal direction when the imaging apparatus is used.

Figure 3:
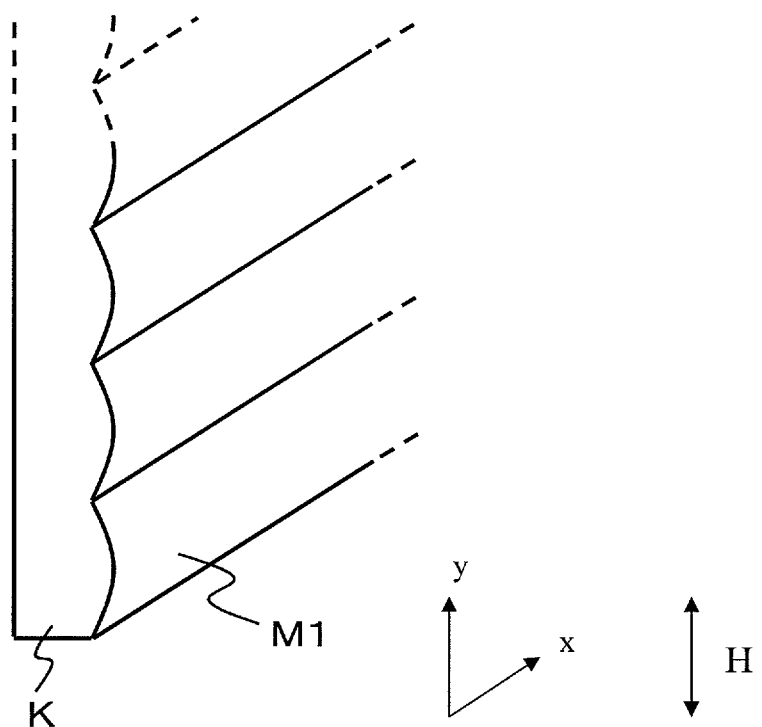
FIG. 3 is a perspective view showing an arrayed optical device K according to Embodiment 1 of the present invention.

FIG. 3 is a perspective view of the arrayed optical device K. The arrayed optical device K includes a plurality of optical elements M1 each having a lens surface. In the present embodiment, the lens surface of each optical element M1 is a cylindrical surface. On one surface of the arrayed optical device K that is closer to the imaging device N, each optical element M1 extends in the x direction (first direction), and a plurality of optical elements M1 are arranged with respect to one another in the y direction (second direction). The y direction corresponds to the horizontal direction in FIGS. 1 and 2. The cross section of each optical element M1 vertical to the x direction has a curved shape protruding toward the imaging device N. Thus, a plurality of optical elements M form a lenticular lens. In the present embodiment, the x direction and the y direction are orthogonal to each other.

As shown in FIG. 1, the arrayed optical device K is arranged in the vicinity of the focal point of the lens optical system L, and is arranged at a position at a predetermined distance from the imaging surface Ni.

FIG. 4(a) is an enlarged view of the arrayed optical device K and the imaging device N shown in FIG. 1, and FIG. 4(b) is a diagram showing the positional relationship between the arrayed optical device K and pixels on the imaging device N. The arrayed optical device K is arranged so that the surface on which the optical elements M1 are formed faces the imaging surface Ni.

The imaging device N includes the imaging surface Ni and a plurality of pixels P. The plurality of pixels P are two-dimensionally arranged in the x direction and the y direction. Where the arrangement in the x direction and that in the y direction are referred to as row and column, respectively, a plurality of pixels are arranged on the imaging surface Ni in m rows and l columns (l and m are each an integer of 2 or more), for example. That is, a group of pixels of one row including 1 to l pixels arranged in the x direction are arranged in m rows in the y direction from the $1^{st}$ row to the $m^{th}$ row.

Of the group of pixels of m rows, the position of the center C'j in the x direction of each of l pixels arranged in the $j^{th}$ row ($1 \leq j < m$) is generally equal to the position of the center C'j+1 in the x direction of each of l pixels arranged in the $j+1^{th}$ row.

Similarly, it can also be seen as if a group of pixels of one column including a plurality of pixels arranged in the y direction were arranged in l columns in the x direction from the 1st column to the $l^{th}$ column. In this case, of the group of pixels of l columns, the position of the center in the y direction of each of m pixels arranged in the $u^{th}$ column ($1 \leq u < l$) is generally equal to the position of the center in the y direction of each of m pixels arranged in the $u+1^{th}$ column.

A plurality of pixels P can be grouped into a plurality of pixels P1 and a plurality of pixels P2, each arranged in the x direction to form a row. The plurality of pixels P1 and the plurality of pixels P2 are each arranged in a single line in the x direction as described above. Rows of pixels P1 and rows of pixels P2 are arranged to alternate with each other in the y direction. The arrayed optical device K is arranged so that one optical element M1 thereof corresponds to two rows of pixels, including a row of pixels P1 and a row or pixels P2 on the imaging surface Ni. A microlens Ms is provided on the imaging surface Ni so as to cover the surface of the pixels P1 and P2.

In the present embodiment, a plurality of first pixels P1 and a plurality of second pixels P2 both have the same shape on the imaging surface Ni. For example, a plurality of first pixels P1 and a plurality of second pixels P2 both have the same rectangular shape and have an equal area.

The arrayed optical device K is designed so that the majority of the light beams (the light beams B1 indicated by a solid line in FIG. 1) having passed through the optical region D1 (shown in FIG. 1, FIG. 2) on the optical device L1p arrives at the pixel P1 on the imaging surface Ni, and the majority of the light beams (the light beams B2 indicated by a broken line in FIG. 1) having passed through the optical region D2 arrives at the pixel P2 on the imaging surface Ni. Specifically, the configuration described above is realized by appropriately setting parameters such as the refractive index of the arrayed optical device K, the distance from the imaging surface Ni, and the radius of curvature at the surface of the optical element M1.

The lens optical system L of the present embodiment is an image-side telecentric optical system. Thus, the primary light beam of the arrayed optical device K is incident with the value of the angle of incidence being close to 0 degree even if the angle of view changes, and it is therefore possible to reduce, across the entire image pickup area, the crosstalk between light beams arriving at the pixel P1 and light beams arriving at the pixel P2.

The stop S is a region through which light beams of all field angles pass. Therefore, by inserting a plane having optical characteristics for controlling polarization characteristics in the vicinity of the stop S, it is possible to similarly control polarization characteristics of light beams of all field angles. That is, in the present embodiment, the optical device L1p may be provided in the vicinity of the stop S. By arranging the optical device L1p in the first and second optical regions D1 and D2 located in the vicinity of the stop, the light beams can be given polarization characteristics according to the number of divisions of regions.

In FIG. 1, the position is such that light having passed through the stop S is incident on the optical device L1p directly (with no other optical members interposed therebetween). The optical device L1p may be provided closer to the object than the stop S. In such a case, light having passed through the optical device L1p may be incident on the stop S directly (with no other optical members interposed therebetween). In the case of an image-side telecentric optical system, the angle of incidence of the light beam at the focal point of the optical system is uniquely determined based on the position of the light beam passing through the stop S. The arrayed optical device K has the function of varying the outgoing direction based on the angle of incidence of the light beam. Therefore, it is possible to distribute light beams among pixels on the imaging surface Ni so as to correspond to the first and second optical regions D1 and D2 divided in the vicinity of the stop S.

Note that in the case of an image-side non-telecentric optical system, the angle of incidence of the light beam at the focal point of the optical system is uniquely determined based on the position of the light beam passing through the stop S and the field angle.

With the configuration described above, it is possible to generate image information having polarization information and non-polarized image information having no polarization information using the brightness information of the pixels P1 and P2, respectively. Since two images are obtained by separating light beams passing through regions in the vicinity of the stop S, it is possible to reduce the parallax as compared with an imaging apparatus having a conventional compound eye configuration.

That is, with the imaging apparatus A, it is possible to obtain a plurality of pieces of image information with little parallax therebetween which are formed by polarized light and non-polarized light, with a single image pickup optical system and through a single iteration of image capture.

With the configuration of the present embodiment, since it is possible to simultaneously obtain these images, these images can be switched from one to another or combined together in accordance with the image information. Such an approach can be applied to the detection of a lane of a road, for example. When detecting a lane of a wet road, unnecessary reflection occurs on a non-polarized image having no polarization information, making it difficult to recognize a lane. On the other hand, with an image obtained through a polarization filter, unnecessary reflection can be reduced, thereby making it easier to recognize a lane. Utilizing such characteristics, road surface circumstances are estimated from image information having polarization information and non-polarized image information having no polarization information, and images are switched from one to another or combined together based on the estimated information, thus making it possible to generate an image with which it is easy to detect a lane.

Note that in the present embodiment, every other pixel value in the y direction is missing. Therefore, the pixel value of the missing pixel may be generated by interpolation using pixel values of adjacent pixels in the y direction, or each pixel value in the x direction may be generated through addition of two pixels.

The configuration may be such that the aspect ratio between the x direction and the y direction of each pixel of the imaging device is 2:1. Such a configuration eliminates the need for such an interpolation operation or addition operation described above.

While the second optical region D2 is a glass plate in the present embodiment, it may be replaced by a filter that attenuates the amount of light such as an ND filter. Since the optical transmittance of a polarization filter is less than 50%, the brightness of an image captured through a second optical region where a glass plate is arranged is twice or more that of an image captured through a first optical region where a polarization filter is arranged. With such a configuration, since the amount of exposure is adjusted so as to match one of the images that has the wider dynamic range, the dynamic range of the image captured through a polarization filter is less than one half that of the image captured through a glass. On the other hand, by replacing the glass plate with an ND filter having an equal transmittance to that of a polarization filter, it is possible to reduce the difference in the amount of exposure between images captured through two regions, and it is possible to effectively ensure the dynamic range for both images.

Embodiment 2

Figure 5:
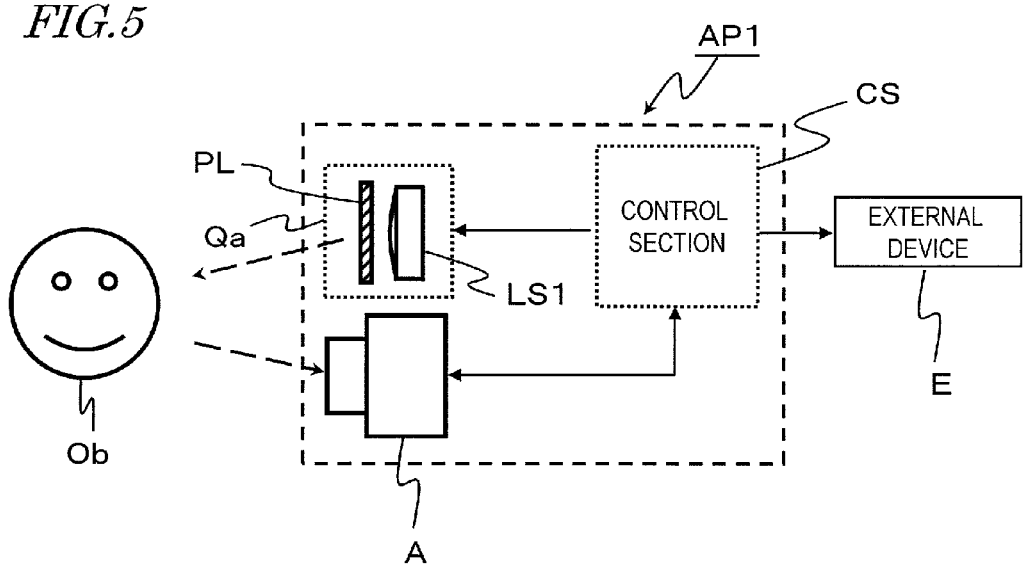
FIG. 5 is a schematic diagram showing an imaging system AP1 according to Embodiment 2 of the present invention.

FIG. 5 is a schematic diagram showing an imaging system AP1 of Embodiment 2. The imaging system AP1 of the present embodiment is formed by the imaging apparatus A of Embodiment 1, a polarized illumination Qa, and a control section CS. The polarized illumination Qa is formed by a light source LS1 for emitting visible light, and a polarization filter PL. The polarization axis of the polarization filter PL has a second polarization axis orthogonal to the polarization axis of the first optical region D1 of the imaging apparatus A. The control section CS controls the imaging apparatus A and the polarized illumination Qa, and performs an input/output control of an external device E, etc. The external device E is, for example, a monitor for displaying an image output from the imaging system AP1, a personal computer for processing an image, or the like.

Light emitted from the light source LS1 passes through the polarization filter PL and arrives at an object Ob. The polarization filter PL primarily transmits light beams oscillating in the direction parallel to the second polarization axis, and absorbs the majority of the light beams oscillating in other directions (e.g., light beams oscillating in the direction orthogonal to the second polarization axis). Therefore, the object Ob is irradiated with only light beams oscillating in the direction of the second polarization axis.

The object Ob is, for example, a living body such as human face skin. The present embodiment will be described while assuming that the object Ob is human face skin. Light having arrived at the face skin (the object Ob) has a component to be reflected and a component to be absorbed, and the imaging apparatus A captures an image of light of the reflected component. Light reflected by the face skin includes a component to be reflected at the surface of the face skin, and a component that enters the inside of the face skin and is repeatedly scattered to exit through a position different from the position through which it entered.

Light reflected at the surface of the face skin is further classified into a component to be specularly reflected and a component to be diffusively reflected. The component specularly reflected at the face skin will retain its polarization. The component diffusively reflected at the face skin and the component which enters the inside of the face skin and exits through a different position will be in a non-polarized state where the polarization is disturbed.

The polarization filter arranged in the first optical region D1 of the imaging apparatus A has a polarization axis orthogonal to the polarization axis of the polarization filter PL in the polarized illumination Qa, and therefore cuts off the majority of the light component that is specularly reflected at the face skin. While light diffusively reflected at the surface of the face skin and light that enters the inside of the face skin and exits through a different position are non-polarized light, the polarization filter arranged in the first optical region D1 of the imaging apparatus A passes therethrough a light component, of the non-polarized light component, that is oscillating in the direction of the first polarization axis. That is, image information captured by light having passed through the first optical region D1 includes a light component that has been diffusively reflected at the surface of the face skin and a light component entering the inside of the face skin and exiting through a different position.

On the other hand, since the second optical region D2 of the imaging apparatus A passes therethrough light beams oscillating in every direction, image information captured by light having passed through the second optical region D2 has a light component specularly reflected at the face skin, a light component diffusively reflected at the surface of the face skin, and a light component entering the inside of the face skin and exiting through a different position.

The inside of the face skin as used above refers to the epidermal region, and an area of the epidermal region where a blotch has occurred contains melanin generated therein. Light entering the epidermis is attenuated by melanin, thereby decreasing the brightness of the image in the area where the blotch is. Note however that image information generated by light having passed through the second optical region D2 includes a component specularly reflected by the face skin, and it therefore appears as shine on the face skin, thus making it difficult to recognize a decrease in the brightness due to the blotch. On the other hand, an image generated by light having passed through the first optical region D1 is an image where the majority of the component specularly reflected by the face skin is cut off, i.e., an image where the majority of the shine on the face skin is cut off, thereby making it easier to see the condition of the blotch on the face skin.

It is possible to generate image information having a light component that has been specularly reflected at the surface of the face skin by subtracting image information captured by light having passed through the first optical region D1 of the imaging apparatus A from image information captured by light having passed through the second optical region D2. With image information having a light component that has been specularly reflected at the surface of the face skin, shading due to unevenness of the face skin is conspicuous, thus providing an image with which it is easy to recognize pores, skin texture, fine wrinkles, etc.

With such a configuration, it is possible to obtain an image with which it is easy to recognize the condition of a blotch by light having passed through the first optical region D1 of the imaging apparatus A of the imaging system AP1; it is possible to obtain a normal image of the face skin by light having passed through the second optical region D2; and moreover it is possible to obtain an image with which it is easy to recognize pores and texture of the face skin by using both images.

Note that the polarization axis of the polarization filter PL may be a polarization axis parallel to the polarization axis of the first optical region D1 of the imaging apparatus A. When an image of the face skin is captured with such a configuration, it is possible to obtain an image with which it is easy to recognize pores, skin texture, fine wrinkles, etc., with image information obtained by light having passed through the first optical region D1. It is possible to obtain an image with which it is easy to recognize the condition of a blotch by subtracting image information captured by light having passed through the first optical region D1 from image information captured by light having passed through the second optical region D2 of the imaging apparatus A.

Thus, by using the imaging system AP1 of the present embodiment, it is possible to simultaneously observe the surface and the inside of a living body. The imaging system AP1 is applicable to an apparatus for diagnosing the face skin and for real-time checking of the makeup, and to medical cameras, or the like, such as endoscopes.

Embodiment 3

Embodiment 3 is different from Embodiment 1 in that light beams of different wavelength bands pass through the optical regions D1 and D2 of the imaging apparatus A. Herein, what is substantially the same as Embodiment 1 will not be described in detail.

Figure 6:
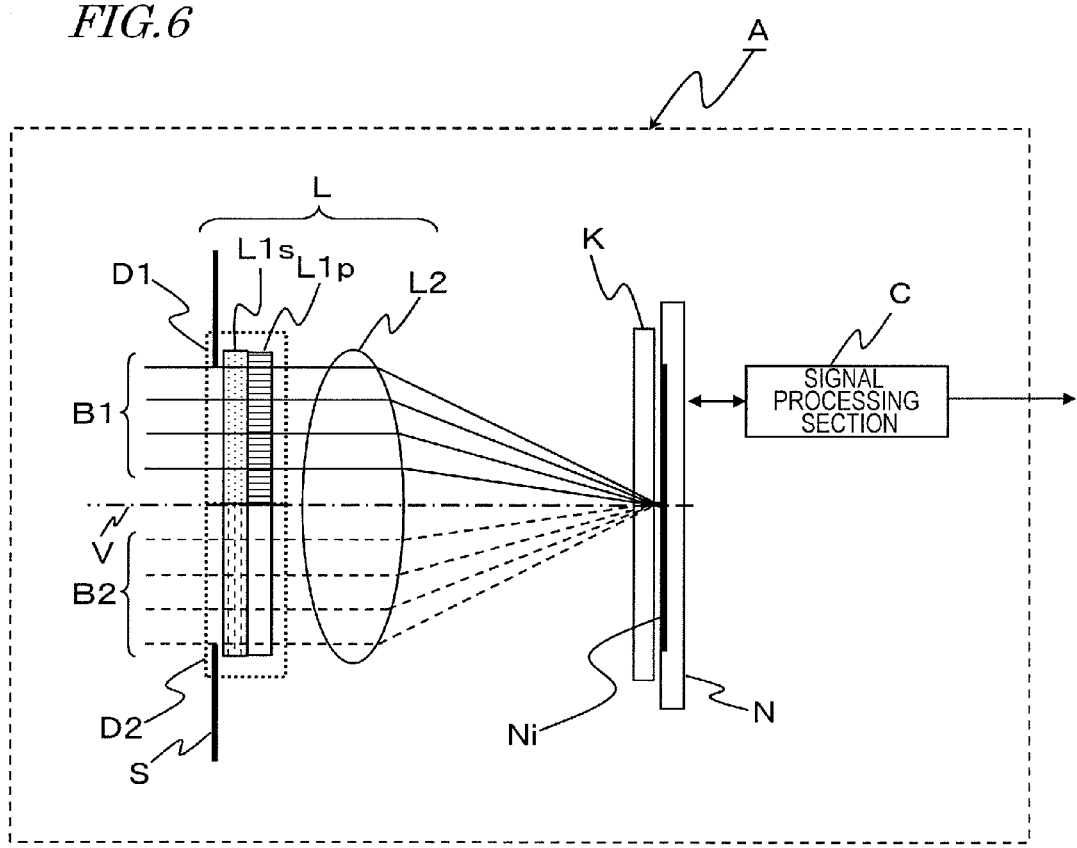
FIG. 6 is a schematic diagram showing Embodiment 3 of the imaging apparatus A according to the present invention.

FIG. 6 is a schematic diagram showing the imaging apparatus A of Embodiment 3. In FIG. 6, the optical device L1s is arranged between the stop S and the optical device L1p. The optical devices L1p and L1s both have portions arranged in the first and second optical regions D1 and D2. A portion of the optical device L1s located in the optical region D1 passes therethrough light of a first wavelength band, and a portion of the optical device L1s located in the optical region D2 passes therethrough light of a second wavelength band. The first wavelength band and the second wavelength band are different wavelength bands from each other.

For example, the "wavelength band" in the "first wavelength band" and the "second wavelength band" refers to a continuous band that accounts for an amount of light of 50% or more of the total amount of light passing through the region, and any wavelength of which 95% or more is cut off passing through the region is not included in the "wavelength band".

Moreover, the two wavelength bands being different from each other means that at least one of the wavelength bands has a band therein that is not included in the other wavelength band. Thus, the wavelength bands may have a partial overlap.

The configuration where transmissive wavelength bands are different from each other is realized by a configuration where a filter using an organic material or a dielectric multilayer film is formed on one surface of the optical device L1s that is closer to the stop S, a configuration where an absorptive-type filter is formed, or a configuration where each region of the optical device L1s is dyed using dye-type filters. Such color filters may be formed on a single flat plate, or may be formed on a plurality of flat plates separated from one another corresponding to different regions. Note that the optical devices L1p and L1s may be in contact with each other or separated from each other. The optical devices L1p and L1s may be bonded together.

In the present embodiment, the signal processing section C of FIG. 6 generates and outputs image information corresponding to a light beam oscillating in the direction of the first polarization axis in the first wavelength band from brightness values obtained from pixels P1, and generates and outputs image information corresponding to a non-polarized light beam in the second wavelength band from brightness values obtained from pixels P2.

In FIG. 6, light beams B1 are light beams passing through the optical region D1 formed by an upper half of the optical device L1s and an upper half of the optical device L1p, and light beams B2 are light beams passing through the optical region D2 formed by a lower half of the optical device L1s and a lower half of the optical device L1p. The light beams B1 and B2 pass through the stop S, the optical device L1s, the optical device L1p, the lens L2 and the arrayed optical device K in this order to arrive at the imaging surface Ni on the imaging device N.

Figure 7:
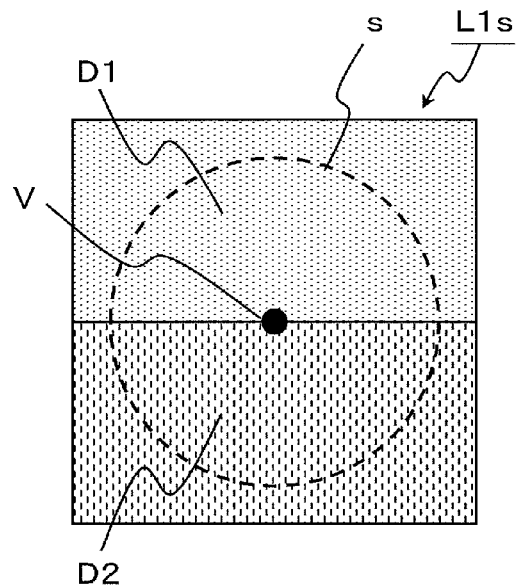
FIG. 7 is a front view showing first and second optical regions D1 and D2 of an optical device L1$s$ according to Embodiment 3 of the present invention, as seen from the object side.

FIG. 7 is a front view showing the optical regions D1 and D2 of the optical device L1s as seen from the object side. The optical regions D1 and D2 of the optical device L1s are formed by two-fold division in the up-down direction in a plane vertical to the optical axis V with the optical axis V being the center of the boundary. In FIG. 7, the broken line s represents the opening area of the stop S.

The configuration of the optical device L1p, the configuration of the arrayed optical device K, and the configuration of the imaging device N are the same as those of Embodiment 1.

In the present embodiment, the first wavelength band is a band of near-ultraviolet, and the second wavelength band is a band of visible light.

Figure 8:
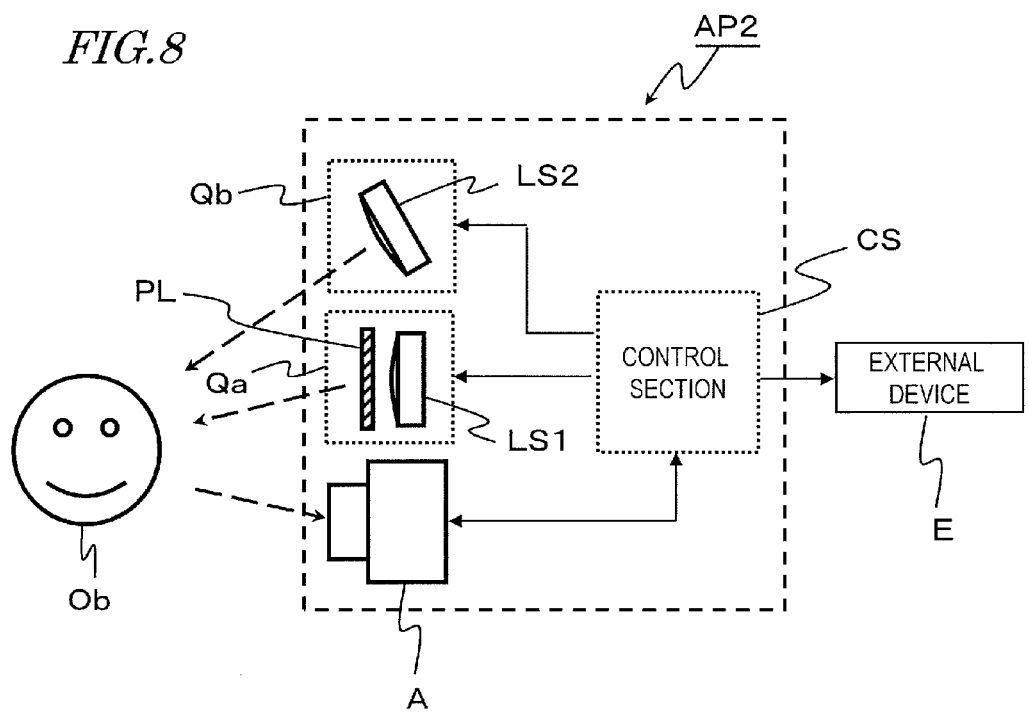
FIG. 8 is a schematic diagram showing an imaging system AP2 according to Embodiment 3 of the present invention.

By using such an imaging apparatus A, it is possible to configure an imaging system as shown in FIG. 8. FIG. 8 is a schematic diagram showing an imaging system AP2 of Embodiment 3. The imaging system AP2 of the present embodiment is different from the imaging system AP1 of Embodiment 2 in that a polarized illumination outputs light of the first wavelength band and that a non-polarized illumination is added that outputs light of a second wavelength band different from the first wavelength band. Herein, what is substantially the same as Embodiment 2 will not be described in detail.

A polarized illumination Qa shown in FIG. 8 is formed by the light source LS1 for outputting near-ultraviolet light, and the polarization filter PL. A non-polarized illumination Qb is formed by a light source LS2 for outputting visible light. Therefore, the object Ob is irradiated with light oscillating in the direction of the second polarization axis in the band of near-ultraviolet light, and non-polarized light oscillating in every direction in the band of visible light.

Light entering the face skin goes into a deeper region of the skin as the wavelength thereof is longer. Light having a short wavelength such as near-ultraviolet light only reaches the epidermal region. Since there is melanin generated by blotches in the epidermal region, light of shorter wavelength will be more attenuated by melanin. Therefore, an image obtained by light of a short wavelength such as near-ultraviolet light is an image with which it is easy to recognize blotches. Although reflected light of specular reflection is generated at the surface of the skin even with light of a short wavelength such as near-ultraviolet light, the specular reflection light can be cut off by the polarization filter arranged in the first optical region of the imaging apparatus A of the present embodiment.

With such a configuration, it is possible to obtain an image with which it is even easier to recognize blotches as compared with Embodiment 2, which image is formed by light having passed through the first optical region D1 of the imaging apparatus A of the imaging system AP2.

Note that the first wavelength band of the filter of the optical device L1s located in the first optical region D1 of the imaging apparatus A and the wavelength band of the light source LS1 do not always need to be the band of near-ultraviolet light. For example, it may be a filter that passes therethrough a predetermined band of the band from 400 nm to 600 nm, such as purple, blue and green, in the visible light band. With such a configuration, the second wavelength band of the filter of the optical device L1s arranged in the second optical region D2 of the imaging apparatus A and the wavelength band of the light source LS2 may be configured so as not to overlap the first wavelength band of the optical device L1s arranged in the optical region D1 and the wavelength band of the light source LS1.

The first wavelength band of the filter of the optical device L1s arranged in the first optical region D1 of the imaging apparatus A and the wavelength band of the light source LS1 may be a wavelength band of near-infrared light. The wavelength of near-infrared light reaches a deep portion of a living body such as face skin. While there are blood vessels in a living body deep part, hemoglobin included in blood absorbs near-infrared light, thereby decreasing the brightness of the image information. Therefore, by utilizing the wavelength band of near-infrared light, it is possible to obtain image information of blood vessels in a deep portion of a living body.

While one polarized illumination Qa and one non-polarized illumination Qb are shown in FIG. 8, a plurality of these may be provided, or they may be arranged alternately in an array pattern.

The illumination of the imaging system AP2 may be formed only by a polarized illumination. In such a case, the light source is formed by a light source emitting light of the first wavelength band and light of the second wavelength band.

The polarized illumination may be formed by two polarized illuminations whose transmission polarization axes are orthogonal to each other. In such a case, the light sources are formed by light sources emitting light of the first wavelength band and light of the second wavelength band, and the two polarized illuminations are switched from one to another as necessary.

Embodiment 4

Embodiment 4 is different from Embodiment 1 in that an optical device L1 of FIG. 1 is divided into three regions and that a region is added that passes therethrough light having the second polarization axis different from the first polarization axis.

Figure 9:
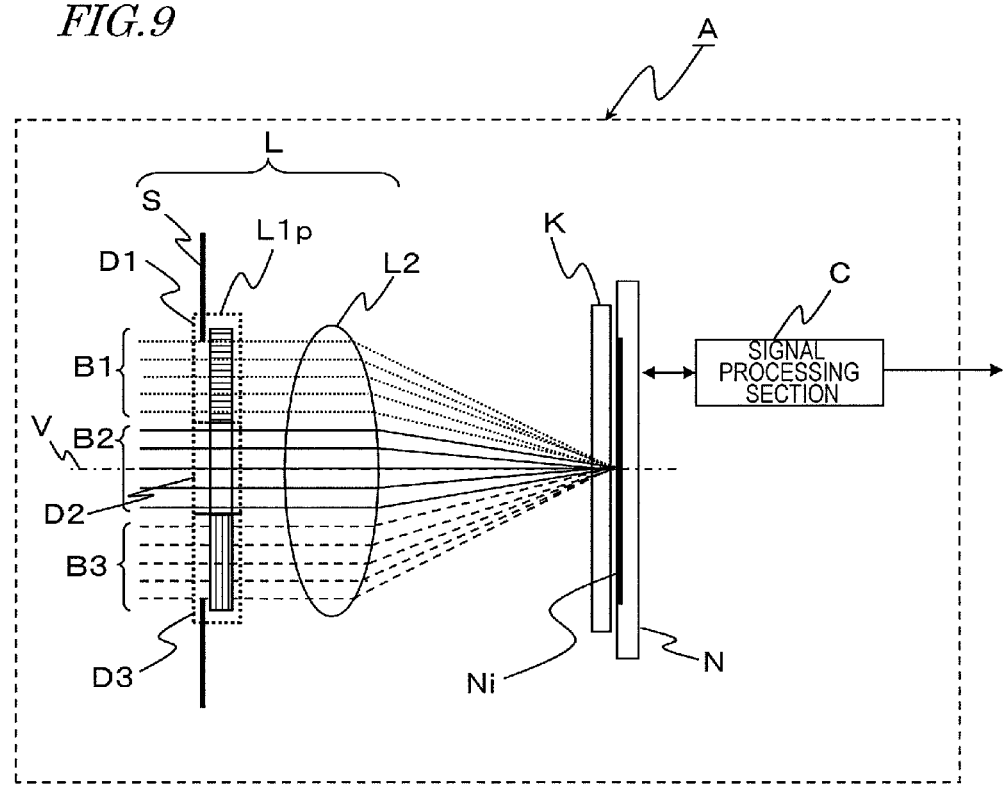
FIG. 9 is a schematic diagram showing Embodiment 4 of the imaging apparatus A according to the present invention.

FIG. 9 is a schematic diagram showing the imaging apparatus A of Embodiment 4.

Figure 11:
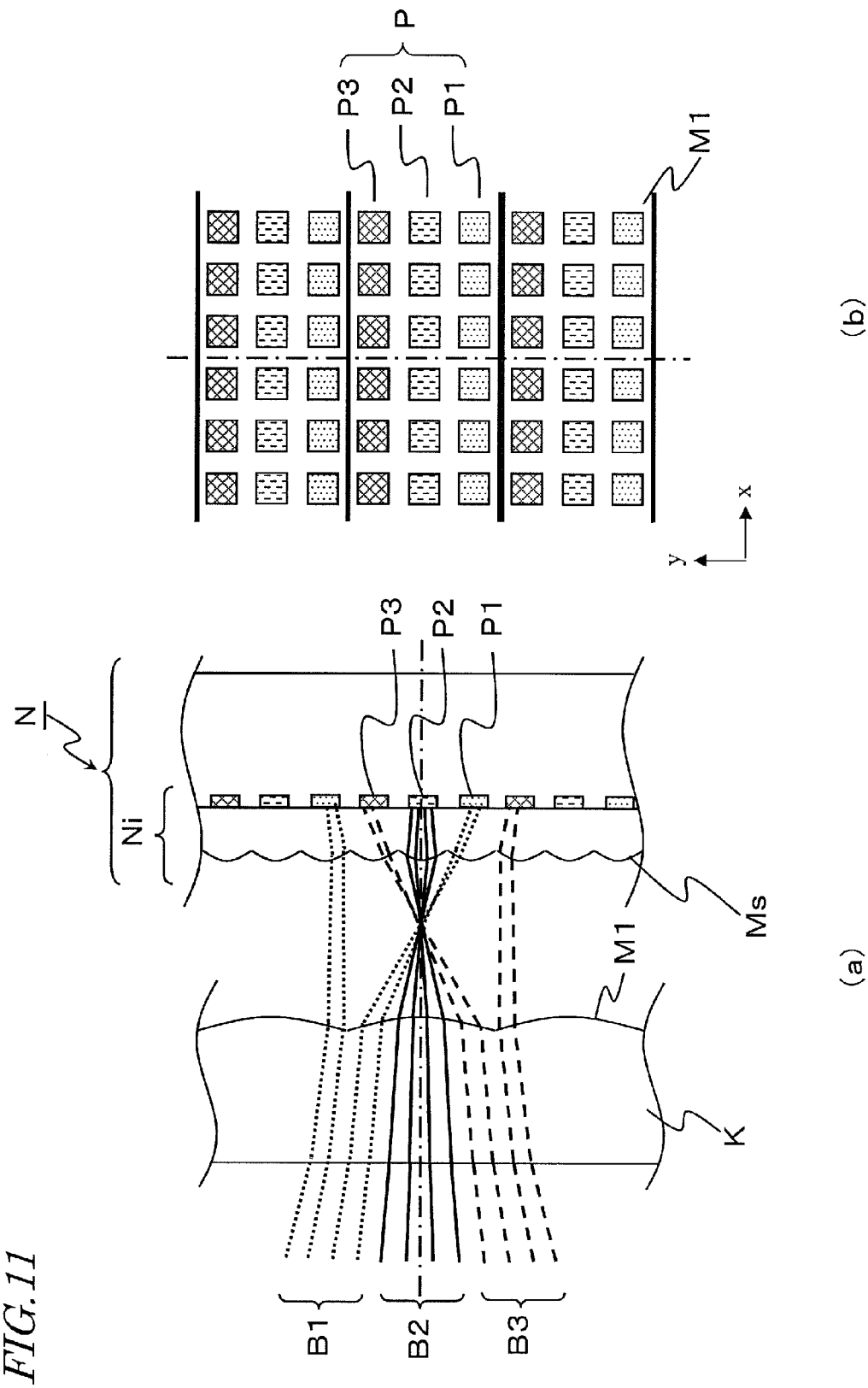
FIG. 11($a$) is an enlarged view of the arrayed optical device K and the imaging device N shown in FIG. 8 according to Embodiment 4 of the present invention, and FIG. 11($b$) is a diagram showing the positional relationship between the arrayed optical device K and pixels on the imaging device N.

In FIG. 9, light beams B1 are light beams passing through the optical region D1 on the optical device L1, light beams B2 are light beams passing through the optical region D2 on the optical device L1, and light beams B3 are light beams passing through the optical region D3 on the optical device L1. The light beams B1, B2 and B3 pass through the stop S, the optical device L1p, the lens L2 and the arrayed optical device K in this order to arrive at the imaging surface Ni on the imaging device N (shown in FIG. 11, etc.).

In FIG. 9, a polarization filter that primarily passes therethrough light oscillating in the direction of the first polarization axis is arranged in the first optical region D1, a glass plate that passes therethrough light oscillating in every direction is arranged in the second optical region D2, and a polarization filter that primarily passes therethrough light oscillating in the direction of the second polarization axis orthogonal to the first polarization axis is arranged in the third optical region D3.

Figure 10:
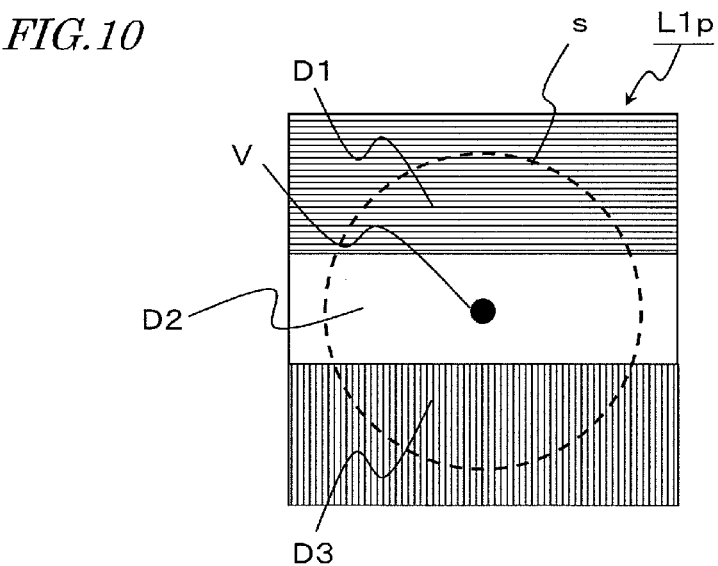
FIG. 10 is a front view showing first, second and third optical regions D1, D2 and D3 of the optical device L1$p$ according to Embodiment 4 of the present invention, as seen from the object side.

FIG. 10 is a front view showing the optical device L1 as seen from the object side, and the first, second and third optical regions D1, D2 and D3 are formed by three-fold division in the up-down direction in a plane vertical to the optical axis V.

FIG. 11(a) is an enlarged view of the arrayed optical device K and the imaging device N shown in FIG. 9, and FIG. 11(b) is a diagram showing the positional relationship between the arrayed optical device K and pixels on the imaging device N. The arrayed optical device K is arranged so that the surface on which the optical elements M1 are formed faces the imaging surface Ni. Pixels P are arranged in a matrix pattern on the imaging surface Ni. The pixels P can be grouped into pixels P1, pixels P2 and pixels P3.

The pixels P1, the pixels P2 and the pixels P3 are each arranged in a row in the x direction. In the y direction, the pixels P1, P2 and P3 are arranged repeatedly. The arrayed optical device K is arranged so that each optical element M1 thereof corresponds to three rows of pixels including one row of pixels P1, one row of pixels P2 and one row of pixels P3 on the imaging surface Ni. The microlens Ms are provided on the imaging surface Ni so as to cover the surface of the pixels P1, P2 and P3.

The arrayed optical device K is designed so that the majority of the light beams B1 (the light beams B1 indicated by a broken line in FIG. 9) having passed through the optical region D1 (shown in FIG. 9, FIG. 10) on the optical device L1 arrives at the pixel P1 on the imaging surface Ni, the majority of the light beams (the light beams B2 indicated by a solid line in FIG. 9) having passed through the optical region D2 arrives at the pixel P2 on the imaging surface Ni, and the majority of the light beams (the light beams B3 indicated by a broken line in FIG. 9) having passed through the optical region D3 arrives at the pixel P3 on the imaging surface Ni. Specifically, the configuration described above is realized by appropriately setting parameters such as the refractive index of the arrayed optical device K, the distance from the imaging surface Ni, and the radius of curvature at the lens surface of the optical element M1.

With such a configuration, the pixel P1, the pixel P2 and the pixel P3 respectively generate image information corresponding to light oscillating in the direction of the first polarization axis, non-polarized image information corresponding to light oscillating in every direction, and image information corresponding to light oscillating in the direction of the second polarization axis orthogonal to the first polarization axis. That is, the imaging apparatus A is capable of obtaining these pieces of image information with a single image pickup optical system and a single iteration of image capture.

In Embodiments 1 and 2, for images having polarization information, there is only one kind of information of light oscillating in the direction of one polarization axis, and the embodiments are therefore limited to applications such as vehicle cameras for the detection of the road surface condition or the lane detection, for example. In Embodiment 4, there are two kinds of polarization axes, and the embodiment is therefore applicable to applications, e.g., surveillance cameras, where it is assumed to be used in a scene where there are glass surfaces of various directions between the camera and the object. For example, while glasses of a building and a windshield of an automobile have reflection surfaces of different normal directions, there are two kinds of polarization axes in the present embodiment, and it is therefore easy to recognize a person beyond a glass of a building or a windshield of an automobile.

Note that the present embodiment may have a configuration where the optical device L1s is added that includes regions through which light beams of different wavelength bands pass for different optical regions as in Embodiment 3. In such a case, there may be one kind of a polarization axis direction.

Embodiment 5

Embodiment 5 is different from Embodiment 3 in that the optical device L1 of FIG. 1 is divided into four regions and that the arrayed optical device is switched from a lenticular lens to a microlens. Herein, what is substantially the same as Embodiment 1 will not be described in detail.

Figure 12:
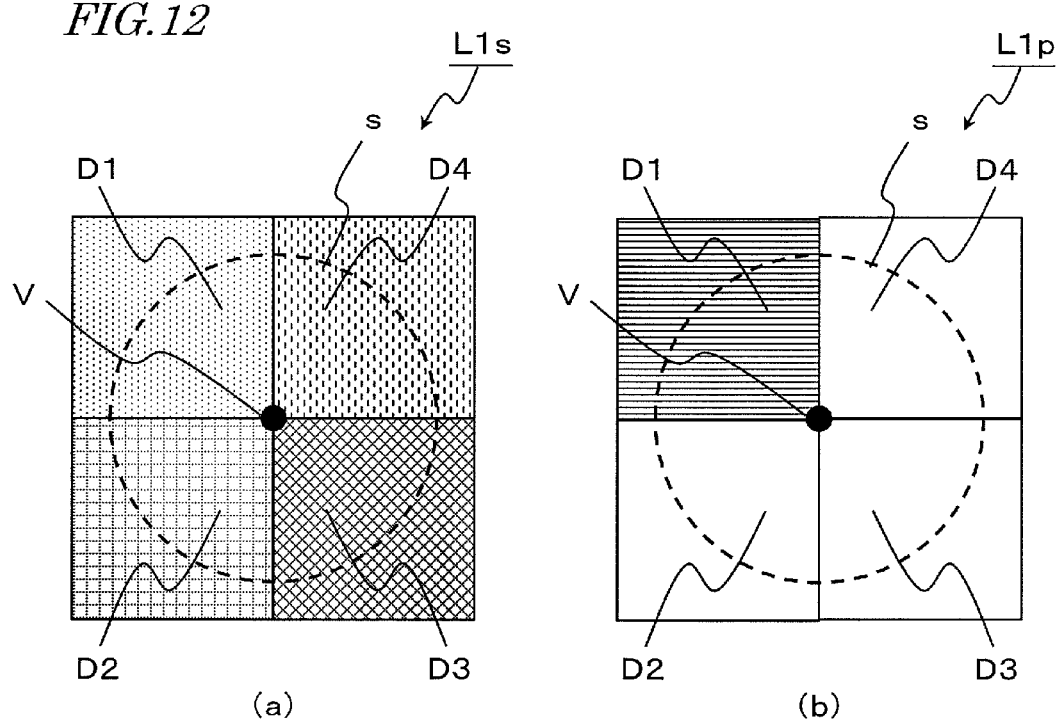
FIG. 12($a$) is a front view showing first, second, third and fourth optical regions D1, D2, D3 and D4 of an optical device L1$s$ according to Embodiment 5 of the present invention, as seen from the object side, and FIG. 12($b$) is a front view showing the first, second, third and fourth optical regions D1, D2, D3 and D4 of the optical device L1p, as seen from the object side.

FIG. 12(a) is a front view showing the optical device L1s as seen from the object side. The optical device L1s is arranged in the first, second, third and fourth optical regions D1, D2, D3 and D4. The first, second, third and fourth optical regions D1, D2, D3 and D4 are formed by four-fold division in the up-down direction and the left-right direction in a plane vertical to the optical axis V with the optical axis V being the center of the boundary. Portions of the optical device L1s located in the first, second, third and fourth optical regions D1, D2, D3 and D4 have different spectral transmittance characteristics from one another. The optical device L1s is arranged between the stop S and the optical device L1p. Arranged in regions of the optical device L1s corresponding to the first, second, third and fourth optical regions D1, D2, D3 and D4 are: a region passing therethrough light beams of the first wavelength band; a region passing therethrough light beams of the second wavelength band; a region passing therethrough light beams of the third wavelength band; and a region passing therethrough light beams of the fourth wavelength band. The first wavelength band, the second wavelength band, the third wavelength band and the fourth wavelength band are different wavelength bands from one another.

FIG. 12(b) is a front view showing the optical device L1p as seen from the object side. The first, second, third and fourth optical regions D1, D2, D3 and D4 are formed by four-fold division in the up-down direction and the left-right direction in a plane vertical to the optical axis V with the optical axis V being the center of the boundary. A polarization filter that passes therethrough light oscillating in the direction of the first polarization axis is arranged only in a portion of the optical device L1p that is located in the first optical region D1, and a glass plate that passes therethrough light oscillating in every direction is arranged in portions thereof located in the other regions.

Figure 13:
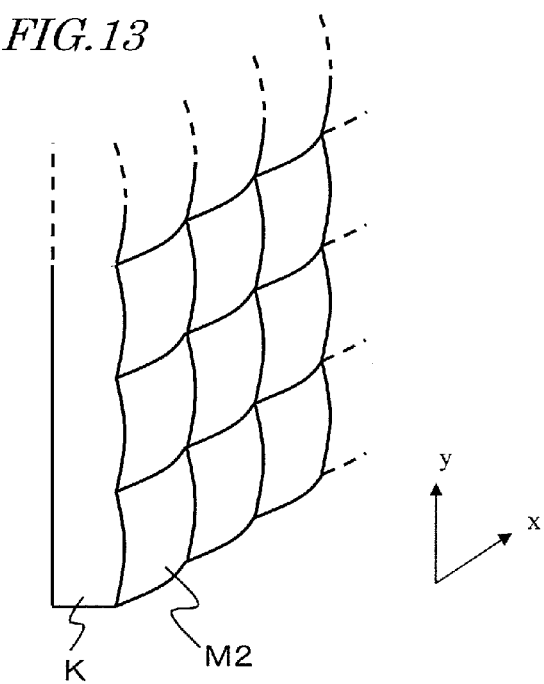
FIG. 13 is a perspective view showing the arrayed optical device K according to Embodiment 5 of the present invention.

FIG. 13 is a perspective view of the arrayed optical device K. Optical elements M2 are arranged in a lattice pattern on one surface of the arrayed optical device K that is closer to the imaging device N. The cross sections (the cross section vertical to the x direction and the cross section vertical to the y direction) of each optical element M2 has a curved shape, and each optical element M2 is protruding toward the imaging device N. Thus, the optical elements M2 are microlenses, and the arrayed optical device K is a microlens array.

Figure 14:
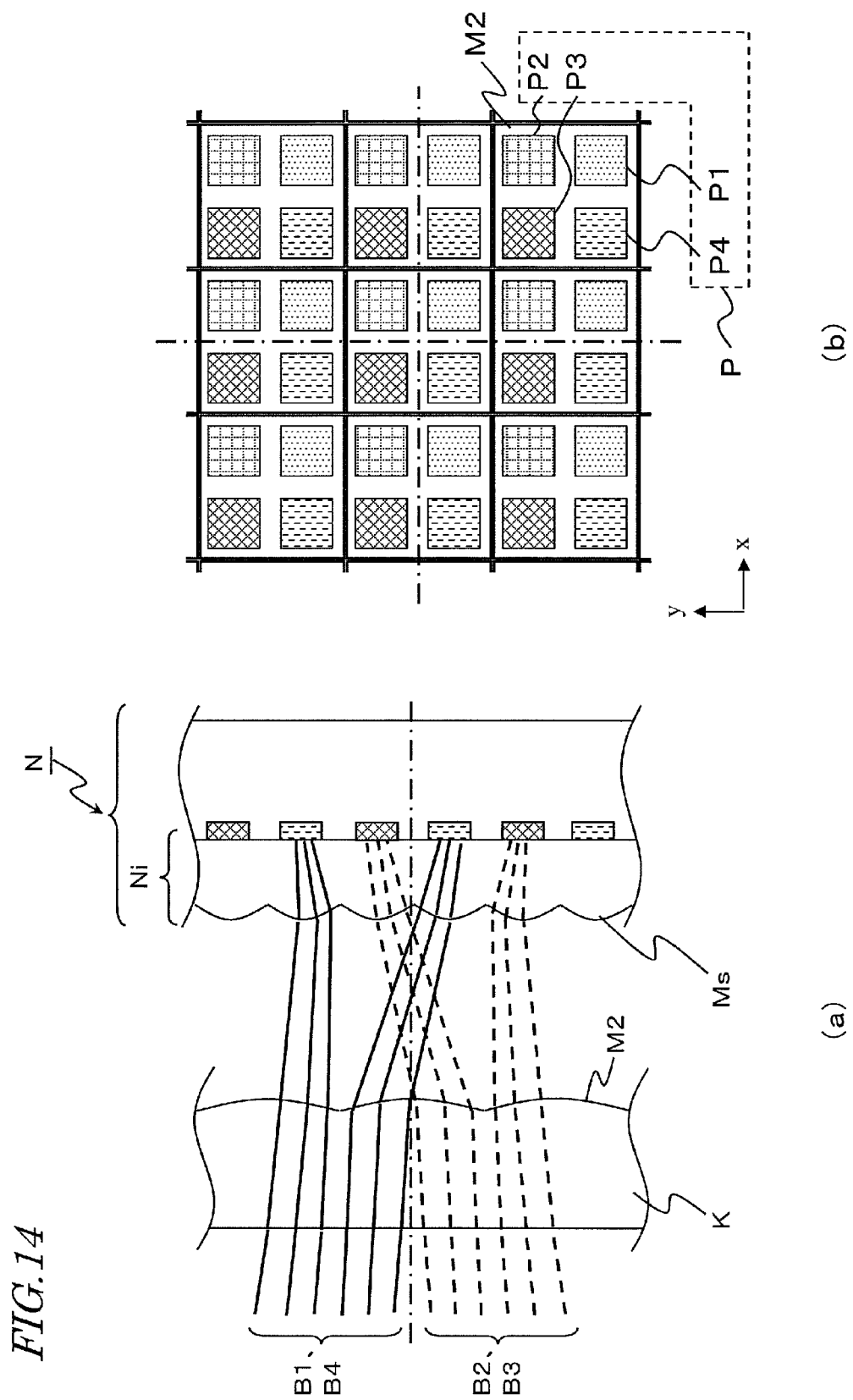
FIG. 14(a) is an enlarged view of the arrayed optical device K and the imaging device N according to Embodiment 5.
FIG. 14(b) is a diagram showing the positional relationship between the arrayed optical device K and pixels on the imaging device N.

FIG. 14(a) is an enlarged view of the arrayed optical device K and the imaging device N, and FIG. 14(b) is a diagram showing the positional relationship between the arrayed optical device K and pixels on the imaging device N. The arrayed optical device K is arranged so that the surface on which the optical elements M2 are formed faces the imaging surface Ni. The pixels P are arranged in a matrix pattern on the imaging surface Ni. The pixels P can be grouped into pixels P1, pixels P2, pixels P3 and pixels P4.

As in Embodiment 1, the arrayed optical device K is arranged in the vicinity of the focal point of the lens optical system L, and is arranged at a position at a predetermined distance from the imaging surface Ni. Microlenses Ms are provided on the imaging surface Ni so as to cover the surface of the pixels P1, P2, P3 and P4.

The arrayed optical device K is arranged so that the surface on which the optical elements M2 are formed faces the imaging surface Ni. The arrayed optical device K is arranged so that each optical element M2 thereof corresponds to two rows and two columns, i.e., four, of pixels P1 to P4 on the imaging surface Ni.

The arrayed optical device K is designed so that the majority of the light beam having passed through the first, second, third and fourth optical regions D1, D2, D3 and D4 formed by the optical devices L1s and L1p arrive at the pixel P1, the pixel P2, the pixel P3 and the pixel P4, respectively, on the imaging surface Ni. Specifically, the configuration described above is realized by appropriately setting parameters such as the refractive index of the arrayed optical device K, the distance from the imaging surface Ni, and the radius of curvature at the surface of the optical element M1.

With such a configuration, the present embodiment generates and outputs image information corresponding to a light beam oscillating in the direction of the first polarization axis in the first wavelength band from brightness values obtained from pixels P1, generates and outputs image information corresponding to a non-polarized light beam in the second wavelength band from brightness values obtained from pixels P2, generates and outputs image information corresponding to a non-polarized light beam in the third wavelength band from brightness values obtained from pixels P3, and generates and outputs image information corresponding to a non-polarized light beam in the fourth wavelength band from brightness values obtained from pixels P4.

In the present embodiment, for example, the first wavelength band in the optical region D1 is a band of near-ultraviolet light, the second wavelength band in the optical region D2 is a band of blue light, the third wavelength band in the optical region D3 is a band of green light, and the fourth wavelength band in the optical region D4 is a band of red light.

By using such an imaging apparatus A, it is possible to configure an imaging system similar to FIG. 8 shown in Embodiment 3. With such a configuration, in the present embodiment, it is possible to obtain an image of near-ultraviolet light having polarization information, and a non-polarized color image composed of three primary colors of blue, green and red.

It is difficult with a non-polarized color image to recognize a blotch due to the shine on the face skin, but an image of near-ultraviolet light having polarization information makes it easier to recognize a blotch. Therefore, by combining these images together, it is possible to generate a color image with which it is easy to recognize a blotch.

Note that while the first wavelength band is a band of near-ultraviolet light in the present embodiment, it may be a filter that passes therethrough a predetermined band of the band from 400 to 600 nm of purple, blue, green, etc., in the visible light band, for example.

Embodiment 6

Embodiment 6 is different from Embodiment 5 in that the first and third optical regions pass therethrough light beams of the same wavelength band. Herein, what is substantially the same as Embodiment 5 will not be described in detail.

Figure 15:
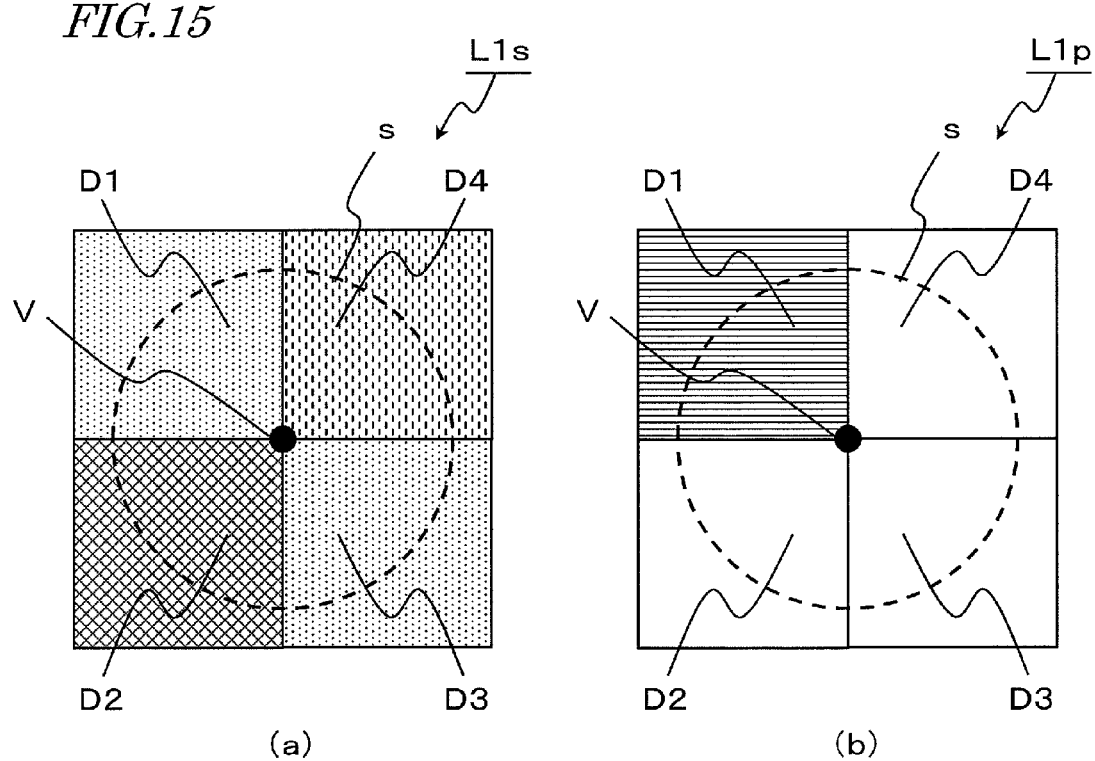
FIG. 15(a) is a front view showing first, second, third and fourth optical regions D1, D2, D3 and D4 of the optical device L1s according to Embodiment 6 of the present invention, as seen from the object side.
FIG. 15(b) is a front view showing first, second, third and fourth optical regions D1, D2, D3 and D4 of the optical device L1p, as seen from the object side.

FIG. 15(a) is a front view of the optical device L1s as seen from the object side. While regions that pass therethrough light beams of all different wavelength bands are provided in regions of the optical device L1s corresponding to the first, second, third and fourth optical regions D1, D2, D3 and D4, respectively, in Embodiment 5, the first and third optical regions D1 and D3 pass therethrough light beams of the same wavelength band in the present embodiment. The second and fourth optical regions D2 and D4 pass therethrough light beams of different wavelength bands from the optical regions D1 and D3, respectively.

FIG. 15(b) is a front view of the optical device L1p as seen from the object side, and the configuration is the same as that of FIG. 12(b) in Embodiment 5.

In the present embodiment, for example, the first wavelength band (the optical regions D1 and D3) is a band of blue light, the second wavelength band (the optical region D2) is a band of green light, and the third wavelength band (the optical region D4) is a band of red light.

By using such an imaging apparatus A, it is possible to configure an imaging system similar to FIG. 8 shown in Embodiment 3. Note however that in the present embodiment, the polarized light Qa of FIG. 8 is formed by the light source LS1 outputting blue light and the polarization filter PL. The non-polarized illumination Qb is formed by the light source LS2 outputting green and red light. With such a configuration, in the present embodiment, it is possible to obtain a blue image having polarization information, and a non-polarized color image composed of three primary colors of blue, green and red.

It is difficult with a non-polarized color image to recognize a blotch due to the shine on the face skin, but a blue image having polarization information makes it easier to recognize a blotch. Therefore, by combining these images together, it is possible to generate a color image with which it is easy to recognize a blotch.

Note that in the present embodiment, the first wavelength band (the optical regions D1 and D3) may be a band of green, the second wavelength band (the optical region D2) may be a band of blue, and the third wavelength band (the optical region D4) may be a band of red.

Figure 16:
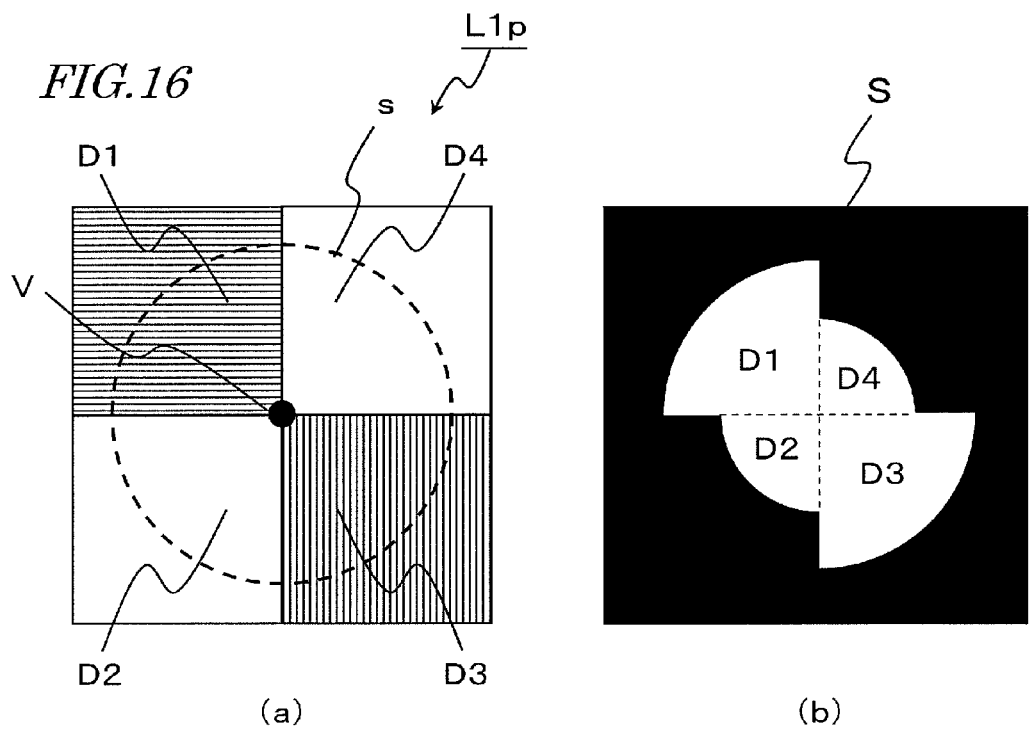
FIG. 16(a) is a front view showing first, second, third and fourth optical regions D1, D2, D3 and D4 of the optical device L1p according to another embodiment of Embodiment 6 of the present invention, as seen from the object side.
FIG. 16(b) is a front view showing first, second, third and fourth optical regions D1, D2, D3 and D4 of a stop S, as seen from the object side.

The present embodiment may employ a configuration where a polarization filter orthogonal to the polarization axis of the polarization filter arranged in the optical region D1 is arranged in the optical region D3 as shown in FIG. 16(a). With light having passed through the optical region D1, the specular reflection component is cut off, and it is therefore possible to obtain image information with which it is easy to recognize a blotch. With light having passed through the optical region D3, it is possible to obtain image information of a specular reflection component. As described in Embodiment 2, with light having been specularly reflected at the surface of the face skin, shading due to unevenness of the face skin is conspicuous, thus making it possible to obtain image information with which it is easy to recognize pores, etc. By combining together these image information and the image information from light beams having passed through the optical regions D2 and D4, it is possible to obtain both a color image with which it is easy to recognize a blotch and a color image with which it is easy to recognize pores, etc.

A configuration may be employed where the area of the optical regions D2 and D4 is made smaller relative to the optical regions D1 and D3 using the stop S as shown in FIG. 16(b). With such a configuration, it is possible to reduce the difference in the amount of exposure between images captured through these regions, and it is possible to effectively ensure the dynamic range for both images. A configuration may be employed where the area of the optical region D3 is made smaller relative to the optical region D1 using the stop S. When capturing an image of a living body such as skin, the specular reflection component may be greater than the scattered reflection light. Therefore, it is possible to reduce the difference in the amount of exposure between an image of the specular reflection component obtained from light beams having passed through the optical region D3 and an image of the scattered reflection light component obtained from light beams having passed through the optical region D1, and it is possible to effectively ensure the dynamic range for both images.

In the present embodiment, since the optical regions D1 and D3 pass therethrough light beams of the same wavelength band, and it is therefore possible to generate non-polarized image information by adding together images from light beams having passed through the optical regions D1 and D3. By combining together these image information and the image information from light beams having passed through the optical regions D2 and D4, it is possible to obtain a non-polarized color image.

Embodiment 7

Embodiment 7 is different from Embodiment 5 in that the optical device L1s is absent and that the imaging device N is a color imaging device. Herein, what is substantially the same as Embodiments 5 and 6 will not be described in detail.

Figure 17:
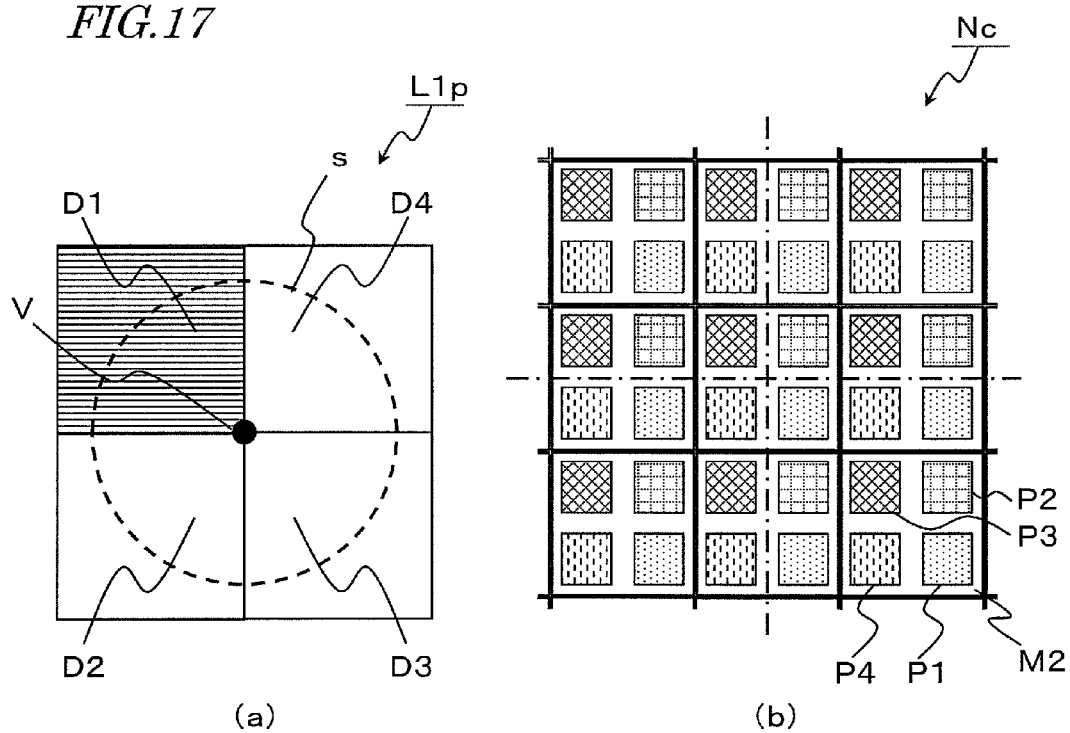
FIG. 17(a) is a front view showing first, second, third and fourth optical regions D1, D2, D3 and D4 of the optical device L1p according to Embodiment 7 of the present invention, as seen from the object side.
FIG. 17(b) is a diagram showing the positional relationship between the arrayed optical device K and pixels on the imaging device N.

FIG. 17(a) is a front view showing the optical device L1p as seen from the object side, and the configuration is the same as those of FIGS. 12(b) and 15(b) shown in Embodiments 5 and 6.

FIG. 17(b) is a diagram showing the positional relationship between the arrayed optical device K and pixels on a color imaging device Nc. The arrayed optical device K is arranged so that the surface on which the optical elements M2 are formed faces the imaging surface Ni. Pixels P are arranged in a matrix pattern on the imaging surface Ni. The pixels P can be grouped into pixels P1, pixels P2, pixels P3 and pixels P4. The pixel P1 is provided with a filter having first spectral transmittance characteristics, and primarily passes therethrough light beams of the purple band while absorbing or reflecting light beams of the other bands. The pixel P2 is provided with a filter having second spectral transmittance characteristics, and primarily passes therethrough light beams of the blue band while absorbing or reflecting light beams of the other bands. The pixel P3 is provided with a filter having third spectral transmittance characteristics, and primarily passes therethrough light beams of the green band while absorbing or reflecting light beams of the other bands. The pixel P4 is provided with a filter having fourth spectral transmittance characteristics, and primarily passes therethrough light beams of the red band while absorbing or reflecting light beams of the other bands.

Since a polarization filter is provided only in the optical region D1 of the optical device L1p, the pixel P1 receives polarized light parallel to the first polarization axis, and the other pixels P2 to P4 receive non-polarized light. Therefore, in the present embodiment, it is possible to obtain a purple image having polarization information, and a non-polarized color image composed of three primary colors of blue, green and red.

In the present embodiment, the spectral function of the optical device L1s of Embodiment 5 is replaced by the color filters for pixels on the color imaging device Nc. With such a configuration, it is possible to obtain advantageous effects similar to those of Embodiment 5.

Figure 18:
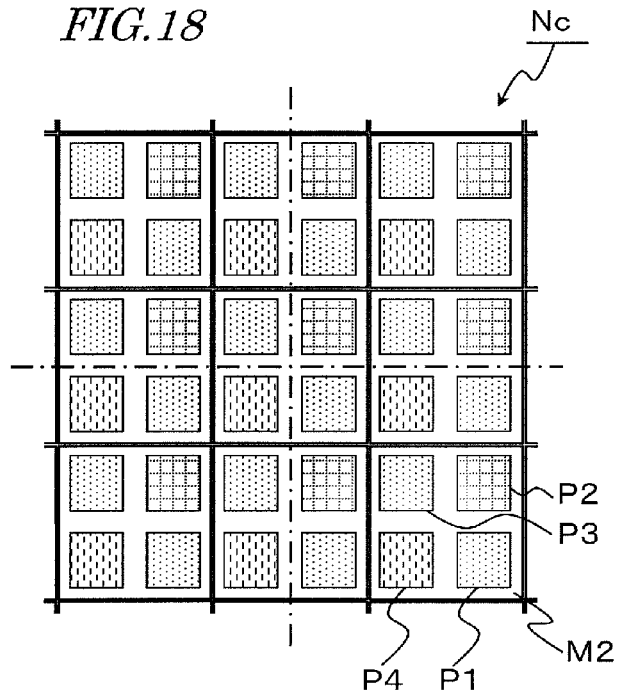
FIG. 18 is a diagram showing the positional relationship between the arrayed optical device K and pixels on the imaging device N according to another embodiment of Embodiment 7 of the present invention.

As shown in FIG. 18, a Bayer array filter may be employed where the pixels P1 and P3 have the same spectral transmittance characteristics. With such a configuration, the optical device L1p may be combined with the configuration of FIG. 12(b) or FIG. 16. With such a configuration, it is possible to obtain advantageous effects similar to those of Embodiment 6.

While the pixel P1 is provided with a filter having the first spectral transmittance characteristics in the present embodiment, the pixel P1 may be provided with no filter and a filter having desirable spectral transmittance characteristics may be provided in the optical region D1, with the optical device L1s without a filter being further provided in the optical regions D2 to D3. In such a case, since the pixel P1 is capable of detecting white light, i.e., light of any wavelength, it is possible to change the wavelength band of polarized light to be detected by the pixel P1 by changing the characteristics of a filter to be provided in the optical region D1 of the optical device L1s. Generally, changing the spectral characteristics of a filter to be provided on the pixel P1 of the color imaging device Nc means to manufacture a color imaging device Nc of different specifications, and it is not easy. In contrast, it is easy to change the characteristics of a filter to be provided in the optical region D1 of the optical device L1s. Therefore, by employing such a structure, it is possible to change the color of an image having polarization information easily and at low cost.

Embodiment 8

Embodiment 8 is a configuration having the optical device L1s that passes therethrough light beams of different wavelength bands between a plurality of optical regions as in Embodiments 3 to 7, and further assumes that the lens L2 is a lens with axial chromatic aberration. With such a configuration, the plurality of optical regions have different levels of optical power in a plane vertical to the optical axis in the vicinity of the stop so that the focus positions of light beams having passed through the plurality of optical regions are substantially equal to each other. The embodiment is different from Embodiments 3 to 7 in this regard. Herein, what is Herein, what is substantially the same as Embodiments 3 to 7 will not be described in detail.

FIG. 19(a) is a diagram schematically showing a ray diagram in Embodiment 8 in a case where the lens L2 is a lens that has axial chromatic aberration due to the wavelength dispersion characteristics of the refractive index as does a single lens. In FIG. 19(a), a filter that passes therethrough light of the first wavelength band is formed in the first optical region D1, and a filter that passes therethrough light of the second wavelength band, relatively longer than the first wavelength band, is formed in the second optical region D2. Since the lens L2 is a lens that has axial chromatic aberration due to the wavelength dispersion characteristics of the refractive index, as does a single lens, for example, light having a longer wavelength is focused farther away from the lens. Therefore, if the settings are such that light beams having passed through the optical region D1 are focused on the imaging surface Ni as shown in FIG. 14(a), light beams having passed through the optical region D2 will not yet be focused on the imaging surface Ni.

FIG. 19(b) is a diagram schematically showing a ray diagram for an imaging apparatus of Embodiment 8. In FIG. 19(b), a lens surface with such optical power that light beams having passed through the second optical region D2 having the second spectral transmittance characteristics will focus on the imaging surface Ni is formed. Specifically, while a portion of the stop-side surface of the optical device L1s that is located in the second optical region D2 has a curvature, a portion of the stop-side surface of the optical device L1s that is located in the first optical region D1 is a plane. Note that the optical device L1s is formed by a base of a light-transmissive member such as a glass or a resin, for example, and an optical filter provided on the surface of the base. For example, a shape (a curved surface or a diffraction lens) for varying optical characteristics is provided in a portion of the stop-side surface of the base. Therefore, light beams passing through the first optical region D1 and light beams passing through the second optical region D2 are both focused on the imaging surface Ni. Thus, according to the present embodiment, since the first optical region D1 and the second optical region D2 have different levels of optical power, the focus position of light passing through the first optical region D1 and the focus position of light passing through the second optical region D2 are closer to each other as compared with a case where the first optical region D1 and the second optical region D2 have an equal level of optical power.

Note that the base of the optical device L1s itself may be colored, giving it a function as an optical filter. In such a case, an optical filter does not need to be provided separately because a portion of the base located in the first optical region D1 passes therethrough light of the first wavelength band and a portion of the base located in the second optical region D2 passes therethrough light of the second wavelength band.

In the present embodiment, a structure for varying the optical power may be provided in a portion of the optical device L1s other than the stop-side surface. For example, the optical power may be varied by providing a shape (a curved surface, a diffraction lens) for varying the optical characteristics in a portion of the imaging device-side surface of the optical device L1s.

FIG. 20(a) is a perspective view of the optical device L1s shown in FIG. 19(b). The optical device L1s is formed by a base, and a filter formed on the surface thereof. A portion of the stop-side surface of the base located in the first optical region D1 is a plane (radius of curvature R1=∞), and a filter having the first spectral transmittance characteristics is formed on the plane. A portion of the stop-side surface of the base located in the second optical region D2 is a lens surface (the radius of curvature R2), and a filter having the second spectral transmittance characteristics is formed on the lens surface. Therefore, there is a step on the stop-side surface of the base in the boundary portion between the first optical region D1 and the second optical region D2. Since light beams passing through such a step will be unnecessary light, the stop S preferably has a configuration where a light-blocking region is provided as shown in FIG. 20(b). Note that a light-blocking member may be provided, separately from the stop S, covering the boundary between the first optical region D1 and the second optical region D2 of the base.

While the configuration above is an example with two optical regions, a similar configuration may be used with three optical regions.

FIG. 21(a) is a perspective view showing the optical device L1s where the optical region is divided into three regions. A portion of the stop-side surface of the base of the optical device L1s located in the first optical region D1 is a plane (radius of curvature R1=∞), and a filter having the first spectral transmittance characteristics is formed on the plane. A portion of the stop-side surface of the base of the optical device L1s located in the second optical region D2 is a lens surface (the radius of curvature R2), and a filter having the second spectral transmittance characteristics is formed on the lens surface. A portion of the stop-side surface of the base of the optical device L1s located in the third optical region D3 is a lens surface (the radius of curvature R3), and a filter having the third spectral transmittance characteristics is formed on the lens surface. With such a configuration, there is a step in a portion of the base located at the boundary between optical regions. Since light beams passing through such a step will be unnecessary light, the stop S preferably has a configuration where a light-blocking region is provided as shown in FIG. 21(b).

A light-blocking region can be provided similarly also when the lens optical system has four optical regions.

Figure 22:
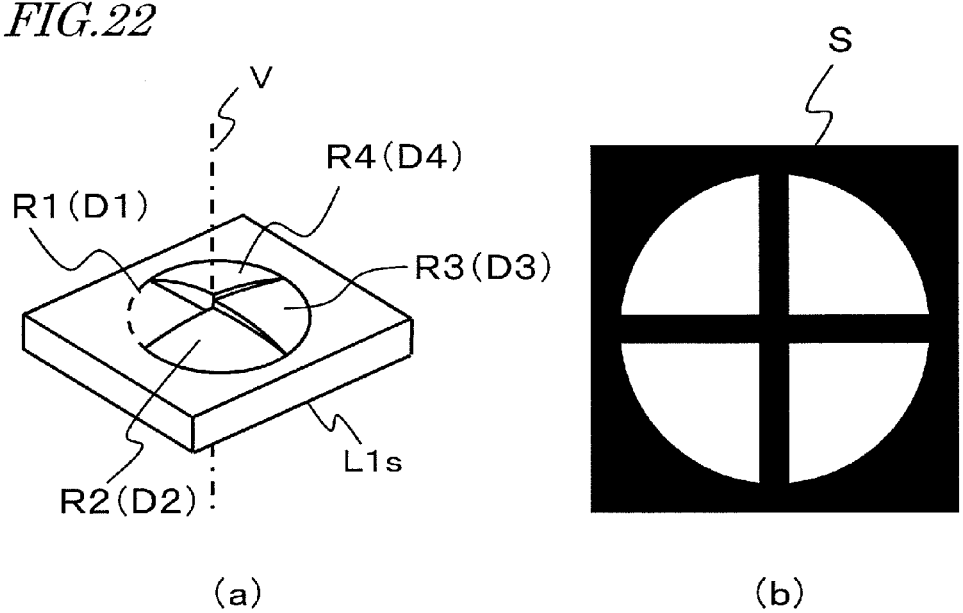
FIG. 22(a) is a perspective view showing the optical device L1s according to another embodiment of Embodiment 8 of the present invention.
FIG. 22(b) is a front view showing the stop S as seen from the object side.

FIG. 22(a) is a perspective view showing the optical device L1s where the optical region is divided into four regions. A portion of the stop-side surface of the base of the optical device L1s located in the first optical region D1 is a plane (radius of curvature R1=∞), and a filter having the first spectral transmittance characteristics is formed on the plane. A portion of the stop-side surface of the base of the optical device L1s located in the second optical region D2 is a lens surface (the radius of curvature R2), and a filter having the second spectral transmittance characteristics is formed on the lens surface. A portion of the stop-side surface of the base of the optical device L1s located in the third optical region D3 is a lens surface (the radius of curvature R3), and a filter having the third spectral transmittance characteristics is formed on the lens surface. A portion of the stop-side surface of the base of the optical device L1s located in the fourth optical region D4 is a lens surface (the radius of curvature R4), and a filter having the fourth spectral transmittance characteristics is formed on the lens surface. With such a configuration, there is a step in a portion of the base located at the boundary between optical regions. Since light beams passing through such a step will be unnecessary light, the stop S preferably has a configuration where a light-blocking region is provided as shown in FIG. 22(b).

Figure 23:
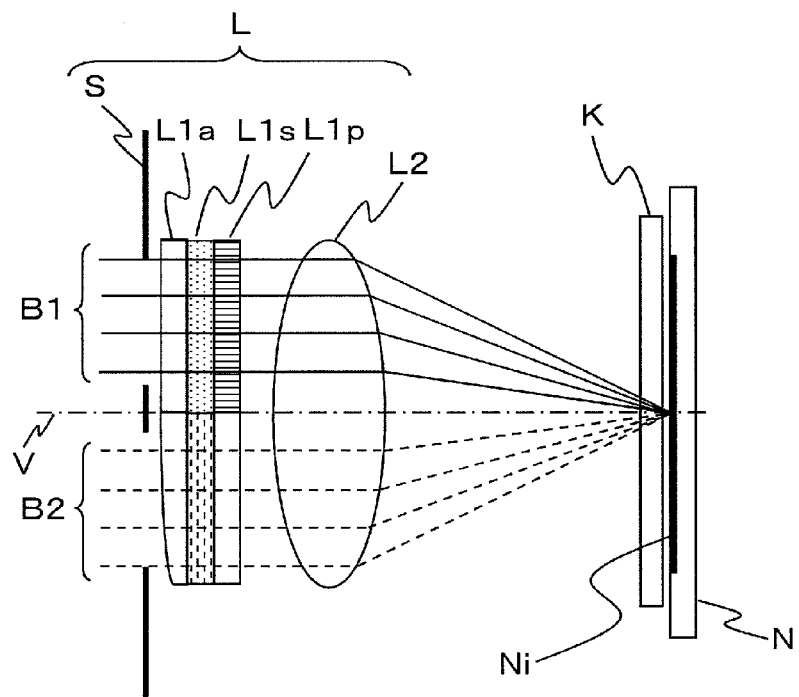
FIG. 23 is a schematic diagram showing an optical system and an imaging section according to another embodiment of Embodiment 8 of the present invention.

FIG. 23 shows an example where a lens capable of varying the optical power for different optical regions is provided, separately from the optical device L1s. In FIG. 23, an optical device L1a, the optical device L1s and the optical device L1p are provided in this order in the direction from the stop toward the imaging device. The optical device L1a, the optical device L1s and the optical device L1p are arranged in the vicinity of the stop. The optical devices L1a, L1s and L1p each have portions located in a plurality of optical regions. Thus, a device having a filter and a lens provided with a lens surface may be separate from each other. The optical devices L1a, L1s and L1p may be arranged in a different order, or they may be arranged on the object side in the vicinity of the stop. They may be arranged separately between the imaging device-side in the vicinity of the stop and the object-side in the vicinity of the stop.

While FIG. 23 is a configuration where the optical region is divided in two, the optical region may be divided in three or divided in four.

As described above, in Embodiment 8, even when the lens L2 is a lens, such as a single lens, whose axial chromatic aberration is not corrected, the axial chromatic aberration can be reduced by providing two regions having different levels of optical power from each other in a plane vertical to the optical axis.

Embodiment 9

Embodiment 9 is different from Embodiments 5, 6 and 7 in that in the area of each microlens, the microlens is rotationally symmetric with respect to the optical axis.

As a method for manufacturing a microlens, there is a method in which a resist is patterned into a rectangular shape, and the curved surface of the lens is formed by heat treatment. A perspective view of such a microlens is as shown in FIG. 24(a1). The contour lines of the microlens of FIG. 24(a1) are as shown in FIG. 24(a2), and the radius of curvature in the x, y direction and that in a diagonal direction are different from each other. FIG. 24(a3) shows the results of light beam tracking simulation in a case where the microlens shown in FIGS. 24(a1) and 24(a2) is used as the arrayed optical device of the present invention. FIG. 24(a3) only shows light beams, of all the light passing through the arrayed optical device K, that pass through one optical region. With such a microlens that is rotationally asymmetric, light leaks to adjacent pixels, causing crosstalk. On the other hand, a perspective view of microlenses each being rotationally symmetric within the square area of the microlens is as shown in FIG. 24(b1). The contour lines of the microlens of FIG. 24(b1) are as shown in FIG. 24(b2), and the radius of curvature in the x, y direction and that in a diagonal direction are equal to each other. Such microlenses can be formed by a thermal imprint or UV imprint method. FIG. 24(b3) shows the results of light beam tracking simulation in a case where the microlens shown in FIGS. 24(b1) and 24(b2) is used as the arrayed optical device of the present invention. FIG. 24(b3) only shows light beams, of all the light passing through the arrayed optical device K, that pass through one optical region. It can be seen that there is no crosstalk as that shown in FIG. 24(a3). Thus, as the lens surface of each optical element of the microlens has a rotationally symmetric shape, it is possible to reduce the crosstalk, and it is therefore possible to suppress crosstalk of color information and crosstalk of polarization information.

Embodiment 10

Embodiment 10 is different from Embodiments 1 to 9 in that a lenticular lens or a microlens array, being an arrayed optical device, is formed on the imaging surface. Herein, what is substantially the same as Embodiments 1 to 9 will not be described in detail.

Figure 25:
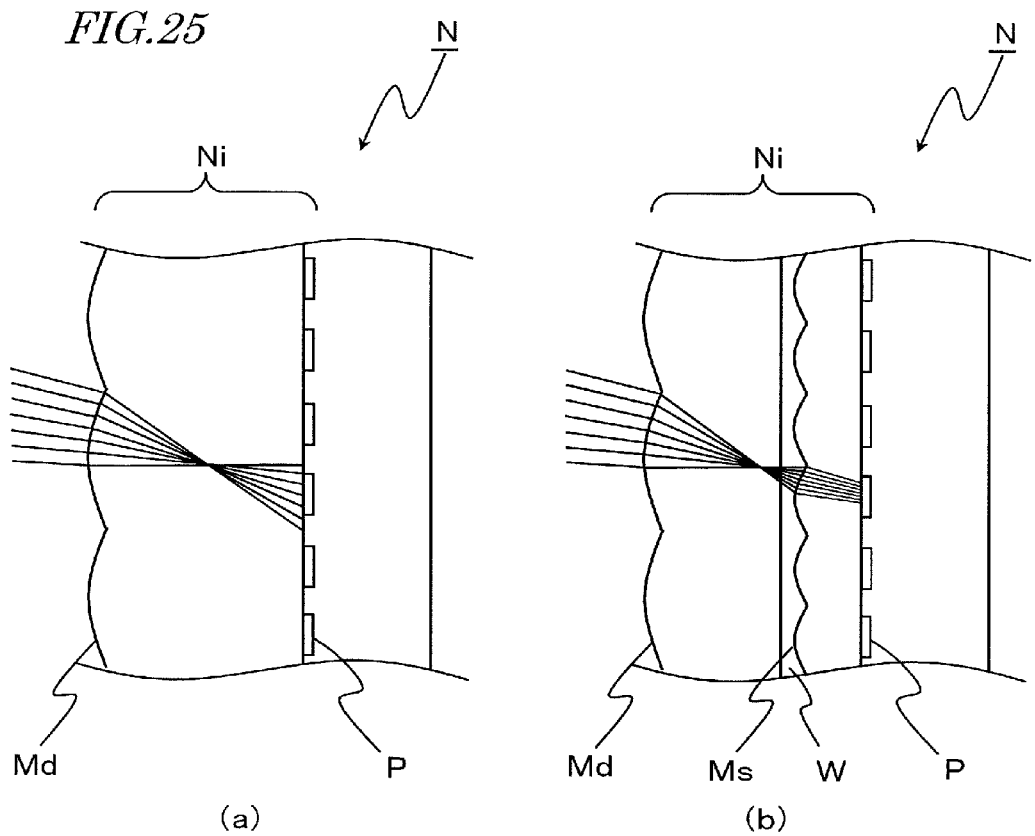
FIGS. 25(a) and 25(b) enlarged views of the arrayed optical device K and the imaging device N according to Embodiment 10 of the present invention.

FIGS. 25(a) and (b) are enlarged views of the arrayed optical device K and the imaging device N, showing only light beams passing through one optical region. In the present embodiment, a lenticular lens (or a microlens array) Md, being the arrayed optical device K, is formed on the imaging surface Ni of the imaging device N. The pixels P are arranged in a matrix pattern, as in Embodiment 1, etc., on the imaging surface Ni. A single lenticular lens optical element or a single microlens corresponds to a plurality of pixels P.

Also in the present embodiment, as in Embodiments 1 to 9, light beams having passed through different optical regions can be guided to different pixels. FIG. 25(b) is a diagram showing a variation of the present embodiment. In the configuration shown in FIG. 25(b), the microlenses Ms are formed on the imaging surface Ni so as to cover the pixels P, and the arrayed optical device is layered on the surface of the microlenses Ms, with a low refractive index layer W interposed therebetween. With the configuration shown in FIG. 25(b), it is possible to increase the light-condensing efficiency as compared with that of the configuration of FIG. 25(a).

When the arrayed optical device is separate from the imaging device as in Embodiments 1 to 9, the alignment between the arrayed optical device and the imaging device is difficult. However, with a configuration where the arrayed optical device K is formed on the imaging device as in the present embodiment, the alignment can be done by the wafer process, thereby making the alignment easier and improving the alignment precision.

Embodiment 11

Figure 26:
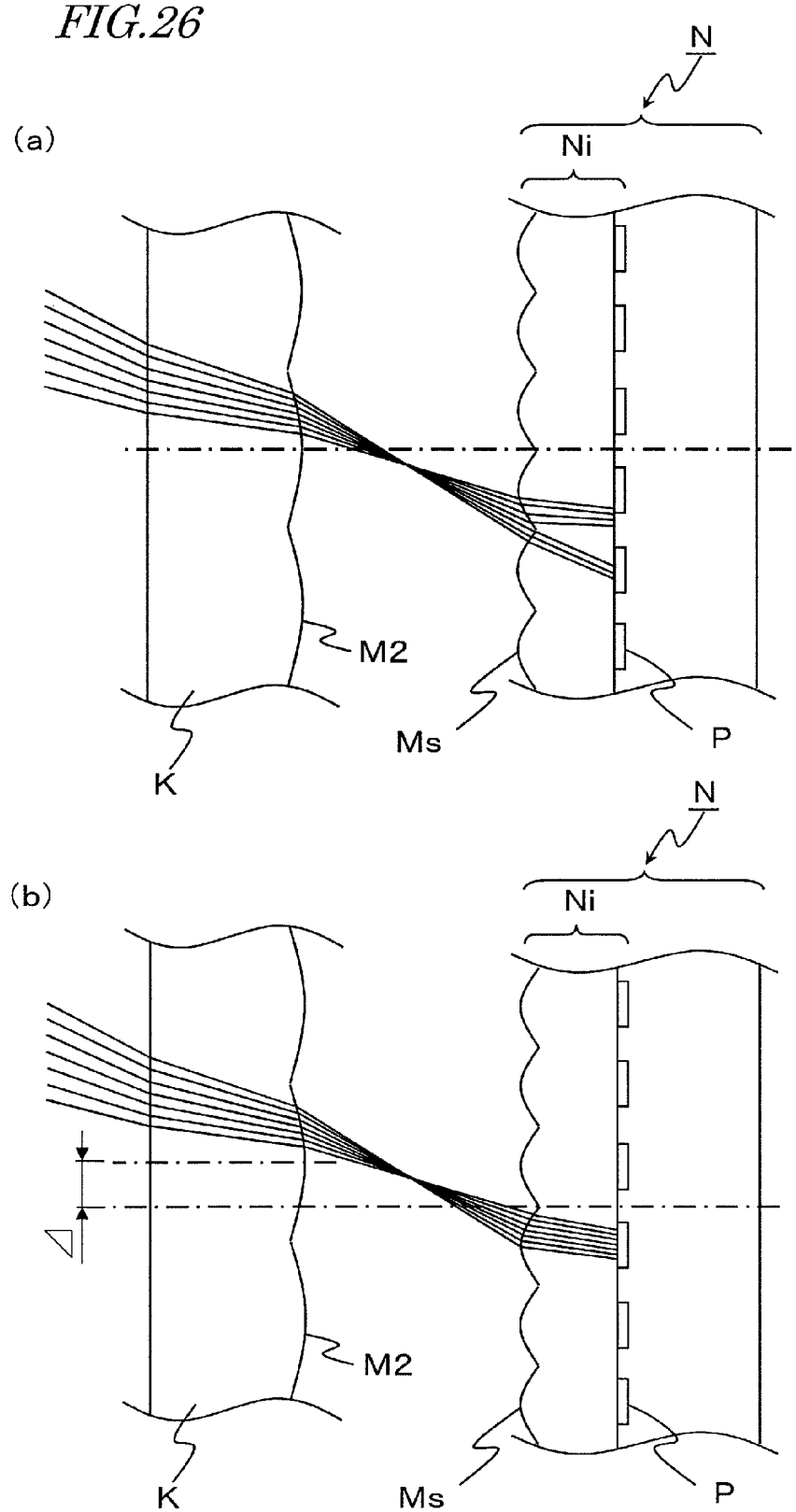
FIGS. 26(a) and 26(b) are enlarged views of the arrayed optical device K and the imaging device N according to Embodiment 11 of the present invention.

Embodiment 11 is different from Embodiments 1 to 10 in that the lens optical system L is an image-side non-telecentric optical system. Many of the lenses used in imaging devices such as cameras use a non-telecentric optical system on the image side. Where an image-side non-telecentric optical system is used for the lens optical system L of an embodiment of the present invention, the primary light beam is incident slantly on the arrayed optical device K if the angle of view changes. FIG. 26(a) is an enlarged view showing the vicinity the imaging section outside the optical axis. FIG. 26(a) shows only the light beams, of all the light passing through the arrayed optical device K, that pass through one optical region. As shown in FIG. 26(a), where the lens optical system L is an image-side non-telecentric optical system, light is likely to leak to adjacent pixels, thereby causing crosstalk. However, by offsetting the arrayed optical device by Δ with respect to the pixel arrangement as shown in FIG. 26(b), it is possible to reduce the crosstalk and to suppress deterioration in color purity. Since the angle of incidence varies depending on the image height, the amount of offset Δ may be set in accordance with the angle of incidence of the light beam on the imaging surface.

By employing an image-side non-telecentric optical system, it is possible to shorten the optical length as compared with an image-side telecentric optical system, and it is therefore possible to reduce the size of the imaging apparatus A.

Embodiment 12

Embodiment 12 is different from Embodiment 1 in that there are two optical regions of the optical device L1p, that a color imaging device having a Bayer-array filter is used, and that optical elements of the arrayed optical device are shifted from one another by half the pitch. Thus, the imaging apparatus of the present embodiment can obtain a color image formed by non-polarized light and a color image formed by polarized light at once.

The imaging apparatus of the present embodiment includes the lens optical system L, the arrayed optical device K, and the imaging device N as shown in FIG. 1. As shown in FIG. 1 and FIG. 2, the lens optical system L includes the optical device L1p having the first optical region D1 and the second optical region D2. Arranged in the first optical region D1 is a polarization filter that passes therethrough light oscillating in the direction of the first polarization axis (transmission axis), and arranged in the second optical region D2 is a glass plate that passes therethrough light oscillating in every direction. Therefore, the light beam B1 having passed through the first optical region D1 is polarized light oscillating in the direction of the first polarization axis (transmission axis). The light beam B2 having passed through the second optical region D2 is non-polarized light.

FIG. 27(a) is an enlarged view of the arrayed optical device K and the imaging device N of the present embodiment. The arrayed optical device K includes a plurality of optical elements M1 and a plurality of optical elements M2, and is arranged so that the surface on which the plurality of optical elements M1 and M2 are formed is facing the imaging surface Ni.

FIG. 27(b) is a diagram showing the positional relationship between the plurality of optical elements M1 and M2 of the arrayed optical device K and pixels on the imaging device N. As in Embodiment 1, the imaging device N includes a plurality of pixels arranged on the imaging surface Ni. As shown in FIG. 27(b), the plurality of pixels are two-dimensionally arranged in the x direction (first direction) and the y direction (second direction). Where the arrangement in the x direction and that in the y direction are referred to as row and column, respectively, a plurality of pixels are arranged on the imaging surface Ni in m rows and l columns (l and m are each an integer of 2 or more), for example. That is, a group of pixels of one row including 1 to l pixels arranged in the x direction are arranged in m rows in the y direction from the $1^{st}$ row to the $m^{th}$ row.

Of the group of pixels of m rows, the position of the center C'j in the x direction of each of l pixels arranged in the $j^{th}$ row ($1 \leq j < m$) is generally equal to the position of the center C'j+1 in the x direction of each of l pixels arranged in the $j+1^{th}$ row.

Similarly, it can also be seen as if a group of pixels of one column including a plurality of pixels arranged in the y direction were arranged in l columns in the x direction from the 1st column to the $l^{th}$ column. In this case, of the group of pixels of l columns, the position of the center in the y direction of each of m pixels arranged in the $u^{th}$ column ($1 \leq u < l$) is generally equal to the position of the center in the y direction of each of m pixels arranged in the $u+1^{th}$ column.

In the present embodiment, the plurality of pixels each have the same shape on the imaging surface Ni in the present embodiment. For example, the plurality of pixels have the same rectangular shape and have an equal area. In the present embodiment, the plurality of pixels are arranged with the same pitch in the x direction and in the y direction.

For the sake of discussion, the plurality of pixels are classified into a plurality of pixels P1A, P2A, P3A, P4A, P1B, P2B, P3B and P4B. One of the plurality of pixels P1A, one of the plurality of pixels P2B, one of the plurality of pixels P3A and one of the plurality of pixels P4B are arranged in two rows and two columns on the imaging surface Ni. These pixels P1A, P2B, P3A, P4B arranged in two rows and two columns are referred to as "a first group of pixels Pg1". One of the plurality of pixels P1B, one of the plurality of pixels P2A, one of the plurality of pixels P3B and one of the plurality of pixels P4A are arranged in two rows and two columns on the imaging surface Ni. These pixels P1B, P2A, P3B, P4A arranged in two rows and two columns are referred to as "a second group of pixels Pg2".

Now, assume that a pixel P3A belonging to the first group of pixels Pg1 is arranged at a position of (p, q). p and q are integers that satisfy $1 \leq p < l$ and $1 \leq q < m$, respectively. In such a case, the remaining pixel P1A, P2B and P4B of the first group of pixels Pg1 are arranged at positions of (p+1, q), (p, q+1) and (p+1, q+1), respectively. The pixels 2A, P1B, P3B and P4A of the second group of pixels Pg2 are arranged at positions of (p+2, q+1), (p+3, q+2), (p+2, q+2) and (p+3, q+1), respectively.

On the surface of the arrayed optical device K that faces the imaging surface Ni, the optical elements M1 are microlenses provided at positions corresponding to the four pixels of the first group of pixels Pg1. Light from the optical elements M1 of the arrayed optical device K is incident on the first group of pixels Pg1. The optical elements M1 make the majority of the light beams having passed through the region D1 incident on the pixels P1A and P3A of the imaging device N, and the majority of light beams having passed through the region D2 incident on the pixels P2B and P4B of the imaging device N.

On the surface of the arrayed optical device K that faces the imaging surface Ni, the optical elements M2 are microlenses provided at positions corresponding to the four pixels of the second group of pixels Pg2. Light from the optical elements M2 of the arrayed optical device K is incident on the second group of pixels Pg2. The optical elements M2 make the majority of the light beams having passed through the region D1 incident on the pixels P2A and P4A of the imaging device N, and the majority of light beams having passed through the region D2 incident on the pixels P1B and P3B of the imaging device N.

A filter having the first spectral transmittance characteristics is provided on the pixels P1A, P2A, P1B and P2B. A filter having the first spectral transmittance characteristics primarily passes therethrough light beams of the green band and absorbs light beams of the other bands. A filter having the second spectral transmittance characteristics is provided on the pixels P3A and P3B. A filter having the second spectral transmittance characteristics primarily passes therethrough light beams of the red band and absorbs light beams of the other bands. A filter having the third spectral transmittance characteristics is provided on the pixels P4A and P4B. A filter having the third spectral transmittance characteristics primarily passes therethrough light beams of the blue band and absorbs light beams of the other bands.

The pixels P1A and P3A (the pixels P1B and P3B, the pixels P2A and P4A, and the pixels P2B and P4B) are arranged alternately in the x direction. The pixels P1A and P4A (the pixels P1B and P4B, the pixels P2A and P3A, and the pixels P2B and P3B) are arranged alternately in the y direction. The pixels P1A, P3A, P1B and P3B are arranged in the same row (arranged in the x direction), the pixels P2A, P4A, P2B and P4B are arranged in the same row (arranged in the y direction), and rows of the pixels P1A, P3A, P1B and P3B and rows of the pixels P2A, P4A, P2B and P4B are arranged alternately in the y direction. Thus, each set of pixels forms a Bayer array. Where pixels are arranged in a Bayer array, the pixels P1A and P2B and the pixels P1B and P2A both having a filter that passes therethrough light of the green band are arranged in diagonal positions in the respective groups of pixels Pg1 and Pg2.

The arrayed optical device K has the function of varying the outgoing direction based on the angle of incidence of the light beam. Therefore, light can be made incident on pixels on the imaging surface Ni so as to correspond to the first optical region D1 and the second optical region D2. In order to ensure that light is incident on such pixels, parameters, such as the refractive index of the arrayed optical device K, the distance from the imaging surface Ni, and the radius of curvature of the surface of the optical elements M1, may be set appropriately, thereby realizing such a configuration as described above.

Next, a specific configuration of the arrayed optical device will be described.

Figure 27:
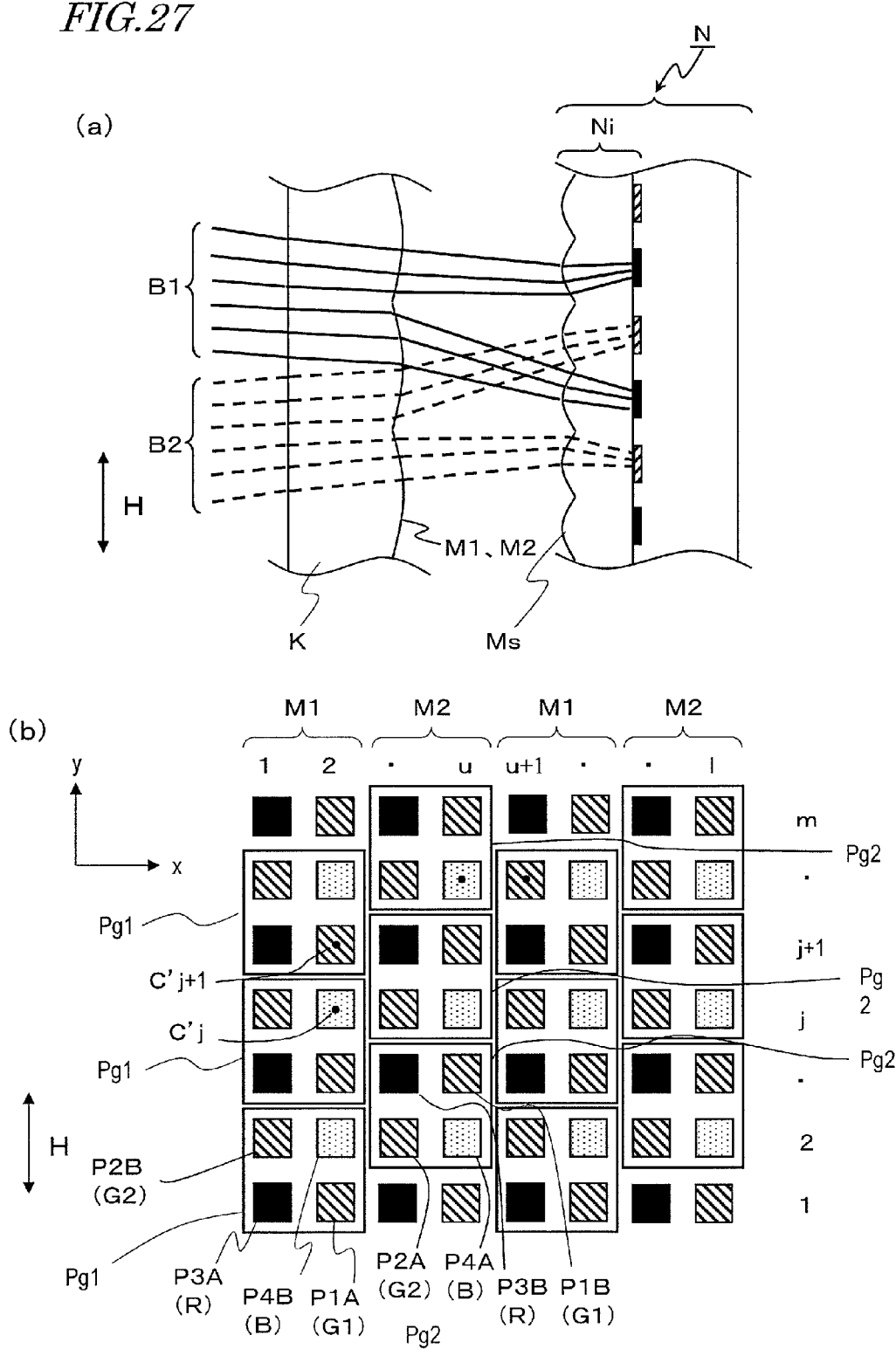
FIG. 27(a) is an enlarged view of the arrayed optical device K and the imaging device N according to Embodiment 12 of the present invention.
FIG. 27(b) is a diagram showing the positional relationship between the arrayed optical device K and pixels on the imaging device N.
Figure 28:
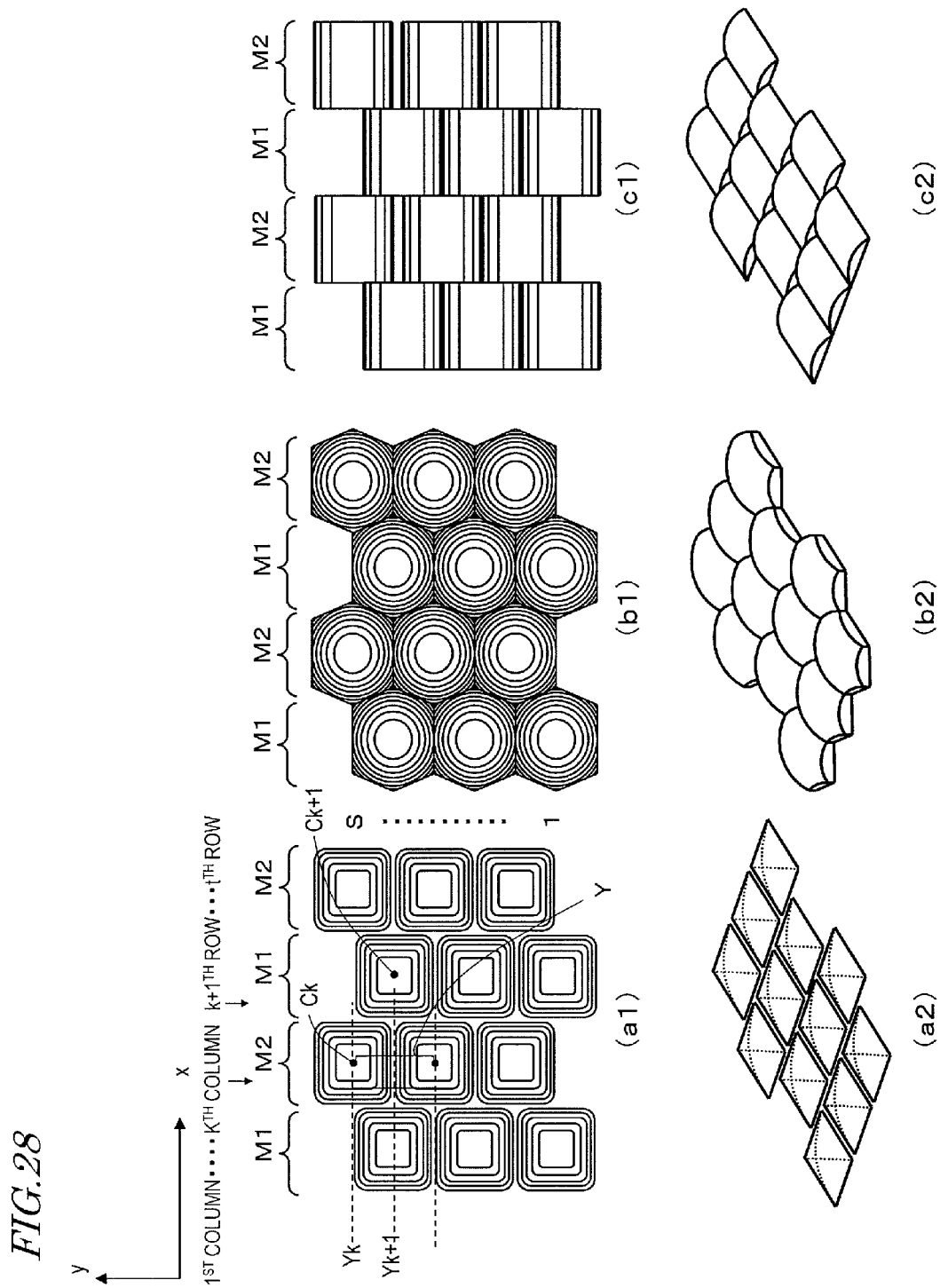
FIG. 28(a1) is a diagram showing an arrangement of a microlens array having a rotationally asymmetric shape with respect to the optical axis and the contour lines thereof.

FIGS. 28(*a*1), 28(*a*2), 28(*b*1), 28(*b*2), 28(*c*1) and 28(*c*2) are diagrams showing shapes and arrangements of the optical elements M1 and M2 shown in FIGS. 27(*a*) and 27(*b*). FIG. 28(*a*1) is a diagram showing an arrangement of optical elements (microlenses) having a rotationally asymmetric shape with respect to the optical axis and the contour lines thereof, and FIG. 28(*a*2) is a perspective view thereof. Such a microlens array formed by forming a quadrangular prism-shaped resist on a glass plate and performing a heat treatment.

As shown in FIG. 28(*a*1), the optical elements M1 and M2 form s (s is an integer greater than or equal to 2) columns each arranged in the y direction on the surface of the arrayed optical device K (e.g., a surface perpendicular to the optical axis of the lens optical system L), and columns of the optical elements M1 and columns of the optical elements M2 are arranged alternately in the x direction. For example, these columns are arranged in t columns, from the first to the $t^{th}$ columns (t is an integer greater than or equal to 2) in the x direction. Where k denotes an arbitrary integer greater than or equal to 1 and less than t (1≤k<t), the position Yk of the center Ck in the y direction of an optical element arranged in the $k^{th}$ column is shifted in the y direction from the position Yk+1 of the center Ck+1 in the column direction of an optical element arranged in the k+1$^{th}$ column. That is, the positions of the centers of the optical element M1 and the optical element M2 are shifted from each other in the y direction.

Now, assume that Y denotes the distance in the column direction between the centers of two optical elements M1 and M2 adjacent to each other in the y column direction on the surface of the arrayed optical device K. The pitches of the optical elements M1 and M2 in the y direction are both Y. In such a case, in the y direction, the shift between the position Yk and the position Yk+1 in the column direction is 0.5Y (half the pitch), for example. Note however that in view of the production errors of the arrayed optical device K, etc., this shift may be 0.45Y or more and 0.55Y or less. If the shift is 0.45Y or more and 0.55Y or less, light beams incident on the first optical region D1 and the second optical region D2 can be directed to intended pixels by means of the arrayed optical device K.

Note that "the center of an optical element in the column direction" is the apex of a solid body of each optical element, for example. Alternatively, it is the midpoint of a line segment connecting together two ends of each optical element in the column direction.

FIG. 28(*b*1) is a diagram showing an arrangement of microlenses having a rotationally symmetric shape with respect to the optical axis and the contour lines thereof, and FIG. 28(*b*2) is a perspective view thereof. The microlenses of FIG. 28(*b*1) are each delimited by a hexagon. Note however that the microlenses are typically not in a regular hexagon since they are formed so as to cover four pixels arranged in a square. While the boundary between microlenses shown in FIGS. 28(*b*1) and 28(*b*2) is delimited by a hexagon, a portion of each microlens that is above the boundary portion may be a spherical surface or an aspherical surface. Such microlenses having a rotationally symmetric shape can be formed on a glass plate, or the like, by a thermal imprint or UV imprint method.

FIG. 28(*c*1) is a diagram showing an arrangement of a microlens array in which every other cylindrical microlenses are shifted by half the pitch and the contour lines thereof, and FIG. 28(*c*2) is a perspective view thereof. The microlens array of FIG. 28(*c*1) can also be formed on a glass plate, or the like, by a thermal imprint or UV imprint method.

FIG. 29(*a*) is a diagram showing the results of a three-dimensional light beam tracking simulation in a case where the microlens shown in FIGS. 28(*a*1) and 28(*a*2) is applied to the arrayed optical device of the present embodiment. While FIG. 29(*a*) only shows light beams passing through the region D1, of all the light beams passing through the arrayed optical device K, light may leak to adjacent pixels to cause crosstalk with such microlenses having a rotationally asymmetric shape due to the difference between the radius of curvature in the longitudinal and lateral directions (directions parallel to four sides of the bottom surface of the microlens) and the radius of curvature in a diagonal direction (the direction of the diagonal line across the bottom surface of the microlens).

FIG. 29(*b*) is a diagram showing the results of a three-dimensional light beam tracking simulation in a case where the microlens shown in FIGS. 28(*b*1) and 28(*b*2) is applied to the arrayed optical device of the present embodiment. While FIG. 29(*b*) only shows light beams passing through one region, of all the light beams passing through the arrayed optical device K, it can be seen that crosstalk such as FIG. 29(*a*) has not occurred. As described above, by forming the optical elements of the arrayed optical device in a rotationally symmetric shape, it is possible to reduce crosstalk between the first color image and the second color image to be described below.

Note that while the microlenses shown in FIGS. 28(*b*1) and 28(*b*2) are hexagonal, they do not always need to be hexagonal as long as they are rotationally symmetric.

FIG. 29(*c*) is a diagram showing the results of a three-dimensional light beam tracking simulation in a case where the cylindrical microlens shown in FIGS. 28(*c*1) and 28(*c*2) is applied to the arrayed optical device of the present embodiment. While FIG. 29(*c*) only shows light beams passing through one region, of all the light beams passing through the arrayed optical device K, it can be seen that crosstalk such as FIG. 29(*a*) has not occurred. As described above, by forming the optical elements of the arrayed optical device in a cylindrical shape, it is possible to reduce crosstalk between the first color image and the second color image.

Next, a method for producing a color image of polarized light and a color image of non-polarized light will be described.

FIGS. 30(*a*) and 30(*b*) are diagrams obtained by extracting only pixels on which light beams having passed through the first optical region D1 and the second optical region D2, respectively, are incident. Since the optical elements M2 are shifted by half the pitch in the y direction with respect to the optical elements M1 as shown in FIG. 28, pixels on which light having passed through the first optical region D1 and the second optical region D2 is incident will each contain color information of red (P3A, or P3B), green (P1A, P2A, or P1B, P2B) and blue (P4A, or P4B).

Note however that light having passed through the first optical region D1 is polarized light parallel to the first optical axis. Therefore, as shown in FIG. 30(*a*), the pixel P3A (red), the pixels P1A and P2A (green) and the pixel P4A (blue) detect polarized light parallel to the first optical axis. On the other hand, as shown in FIG. 30(*b*), the pixel P3B (red), the pixels P1B and P2B (green) and the pixel P4B (blue) detect non-polarized light. Thus, it is possible to generate a color image of polarized light parallel to the first optical axis and a color image of non-polarized light by means of pixels receiving light beams having passed through the first optical region D1 and pixels receiving light beams having passed through the second optical region D2, respectively. Hereinafter, a color image of polarized light parallel to the first optical axis and a color image of non-polarized light will be referred to as a first color image and a second color image.

The first color image and the second color image are generated in the signal processing section C (shown in FIG. 1). The first color image and the second color image are generated based on color information (specifically, brightness information) obtained from pixels shown in FIGS. 30(a) and 30(b), respectively. Since the first and second groups of pixels corresponding to the color images only have one piece of color information for one pixel, as shown in FIGS. 30(a) and 30(b), color information of the other two colors are interpolated from brightness values of surrounding pixels.

For example, with the first color image, only information of green (G2) is present at the position of the pixel P2A of the second group of pixels Pg2 as shown in FIG. 30(a). Therefore, information of red (R) and blue (B) are interpolated from surrounding pixels to obtain information of blue, green and red at the position of the pixel P2A of the second group of pixels Pg2. Specifically, the brightness information of red and blue at P2A of the second group of pixels Pg2 are interpolated from brightness information of red and blue obtained from the pixel P3A and the pixel P4A located in the y direction, the x direction or the diagonal direction. Similarly, brightness information of green and red at the pixel P4A of the second group of pixels Pg2 are obtained by interpolation using brightness information of green and red obtained from the pixel P2A and the pixel P3A located in the y direction, the x direction or the diagonal direction. Brightness information of red and blue at the pixel P1A of the first group of pixels Pg1 and brightness information of green and blue at the pixel P3A of the first group of pixels Pg1 are also obtained by similar interpolation. Thus, it is possible to obtain the first color image.

As shown in FIG. 30(b), also for the second color image, brightness information of red and green at the pixel P4B of the first group of pixels Pg1, brightness information of red and blue at the pixel P2B, brightness information of red and blue at the pixel P1B of the second group of pixels Pg2 and brightness information of green and blue at the pixel P3B can be similarly obtained by interpolation. Thus, it is possible to obtain the second color image.

Note that in each of the first and second color images, the color information in the y direction is partially missing. For example, of the four pixels of the first group of pixels Pg1 of the first color image, the pixel P4B and the pixel P2B are missing. Brightness information of these missing pixels may be generated by interpolation, after the interpolation of colors described above, using brightness values of colors detected in pixels adjacent in the y direction and brightness values of colors obtained by interpolation. Specifically, brightness information of red, blue and green at the pixel P4B and the pixel P2B of the first group of pixels Pg1 may be obtained from brightness information of red, blue and green at the pixel P3A and the pixel P1A adjacent in the y direction.

By such an interpolation process as described above, it is possible to generate a color image of polarized light parallel to the first optical axis and a color image of non-polarized light.

According to the present embodiment, as shown in FIGS. 30(a) and 30(b), in each of the color image of polarized light parallel to the first optical axis and the color image of non-polarized light, each set of adjacent groups of pixels (first groups of pixels Pg1, or second groups of pixels Pg2, or a first group of pixels Pg1 and a second group of pixels Pg2) forms a color image. Thus, the pitch between pixels forming two color images will not be long, and it is therefore possible to obtain a high-resolution image.

According to the present embodiment, it is possible to use an imaging device of a conventional Bayer array type, thus reducing the initial investment as it is possible to eliminate the initial investment such as a photomask for a color filter of a dedicated filter array.

Note that the optical system of the imaging apparatus of the present embodiment may be an image-side telecentric optical system. Thus, the primary light beam is incident on the arrayed optical device K at an angle of incidence close to 0 degree even if the angle of view varies, and it is therefore possible to reduce crosstalk between light beams arriving at the pixels P1A, P1B, P2A, P2B, P3A, P3B, P4A and P4B across the entire image pickup area.

Embodiment 13

Embodiment 13 is a configuration where the imaging system AP2 of Embodiment 3 is applied to a microscope. Note that the imaging apparatus A of the imaging system AP2 to be applied to a microscope of the present embodiment may be any of the imaging apparatuses A of Embodiments 1, 3 to 11.

Figure 31:
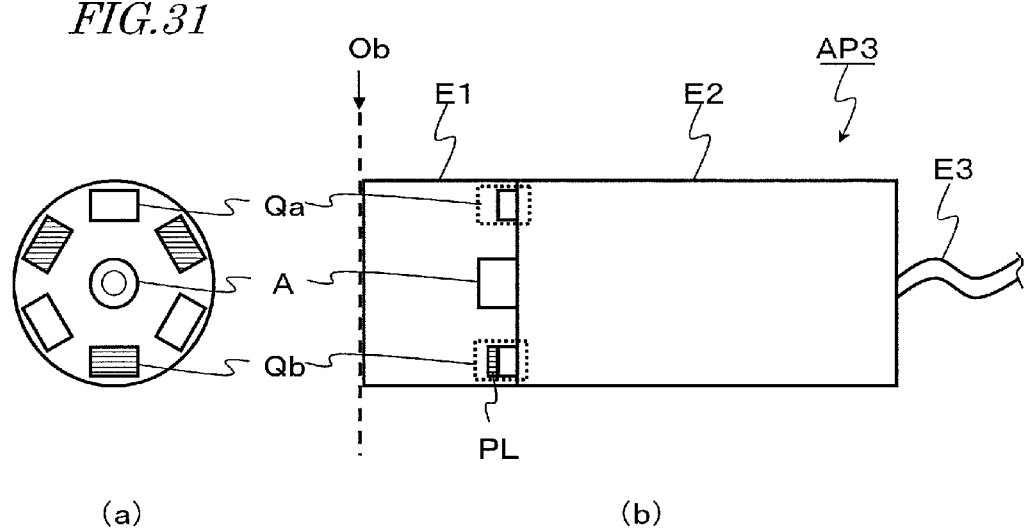
FIG. 31(a) is a front view showing a microscope AP3 according to Embodiment 13 of the present invention.
FIG. 31(b) is a side view.

FIGS. 31(a) and 31(b) are a front view and a side view, respectively, of a microscope AP3 of Embodiment 13. The microscope AP3 is formed by a head section E1, a lens barrel E2 and a cable E3, wherein the lens barrel E2 includes therein the imaging apparatus A, the polarized illumination Qa and the non-polarized illumination Qb.

As shown in FIG. 31(a), the polarized illumination Qa and the non-polarized illumination Qb are arranged alternately in a concentric pattern about the imaging apparatus A. The setting is such that the tip of the head section E1 is the focus position of the imaging apparatus A so that the resolution is highest when the head section E1 is brought into close contact with the object Ob, such as face skin.

The object Ob, such as face skin, is irradiated with light from the polarized illumination Qa and light from the non-polarized illumination Qb, and the imaging apparatus A can therefore simultaneously obtain both image information having polarization information and normal image information from reflected light from the object Ob. The image information obtained by the imaging apparatus A is connected to a monitor, a personal computer, or the like, through the cable E3.

By using such a microscope AP3, it is possible to simultaneously obtain a normal enlarged image, an enlarged image with which it is easy to recognize the condition of a blotch, and an enlarged image with which it is easy to recognize pores and texture of the face skin.

Note that the microscope of Embodiment 13 may be the imaging system AP1 of Embodiment 2. The imaging apparatus A of the imaging system AP1 used for a microscope may be any of the imaging apparatuses A of Embodiments 1 and 3 to 12.

Embodiment 14

Embodiment 14 is a configuration where the imaging system AP2 of Embodiment 3 is applied to a capsule endoscope. Note that the imaging apparatus A of the imaging system AP2 applied to a capsule endoscope may be the imaging apparatus A of Embodiments 1 and 3 to 12.

Figure 32:
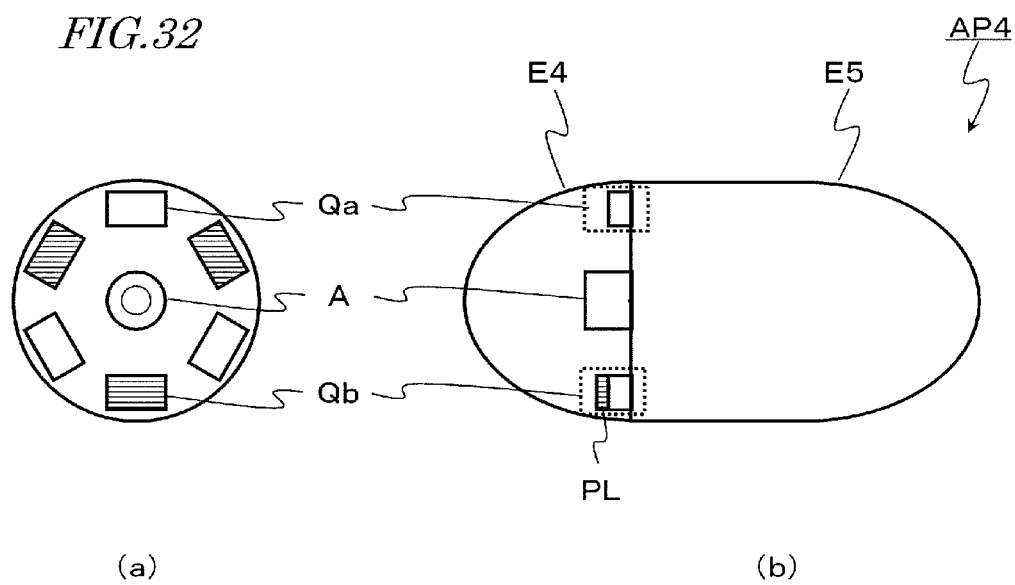
FIG. 32(a) is a front view showing a capsule endoscope AP4 according to Embodiment 14 of the present invention.
FIG. 32(b) is a side view.

FIGS. 32(a) and 32(b) are a front view and a side view, respectively, of the capsule endoscope AP4 of Embodiment 14. The capsule endoscope AP4 includes a dome portion E4 and a lens barrel E5, wherein the lens barrel E5 includes therein the imaging apparatus A, the polarized illumination Qa and the non-polarized illumination Qb. In addition, a battery, a transmitter/receiver IC, a transmitter/receiver antenna, etc., may be provided inside the lens barrel E5.

As shown in FIG. 32(a), the polarized illumination Qa and the non-polarized illumination Qb are arranged alternately in a concentric pattern about the imaging apparatus A.

The object, which is a digestive organ in a living body, is irradiated with light from the polarized illumination Qa and light from the non-polarized illumination Qb, and the imaging apparatus A can therefore simultaneously obtain both image information having polarization information and normal image information from reflected light from the object. The image information obtained by the imaging apparatus A is wirelessly transmitted to an external terminal through a transmitter/receiver IC and a transmitter/receiver antenna.

By using such a capsule endoscope AP4, it is possible to simultaneously obtain a polarized light image with which it is easy to recognize the condition of a digestive organ and a normal image.

Note that the capsule endoscope of Embodiment 14 may be the imaging system AP1 of Embodiment 2. The imaging apparatus A of the imaging system AP1 used for a capsule endoscope may be any of the imaging apparatuses A of Embodiments 1 and 3 to 12.

Embodiment 15

Embodiment 15 is a configuration where the imaging system AP2 of Embodiment 3 is applied to an electronic mirror. Note that the imaging apparatus A in the imaging system AP2 may be the imaging apparatus A of Embodiments 1 and 3 to 12.

FIG. 33(a) is a front view of the electronic mirror AP5. The electronic mirror AP5 includes a frame T1, the frame T1 including therein a display J1, the imaging apparatus A, the polarized illumination Qa and the non-polarized illumination Qb. As shown in FIG. 33(a), the polarized illumination Qa and the non-polarized illumination Qb are arranged alternately in the up-down direction in the left area and in the right area of the display J1.

A human face, which is the object, is irradiated with light from the polarized illumination Qa and light from the non-polarized illumination Qb, and the imaging apparatus A can therefore simultaneously obtain both image information having polarization information and normal image information from reflected light from the human, who is the object. The image information obtained by the imaging apparatus A is displayed in real time on the display J1 while being inverted left and right.

By using such an electronic mirror AP5, it is possible to simultaneously obtain a normal image, an image with which it is easy to recognize the condition of a blotch, and an image with which it is easy to recognize pores and texture of face skin, and the user himself/herself, who is the object, can use it to check the mirror image of the user himself/herself as if it were a normal mirror. The configuration may be such that the user can switch as necessary between the normal image, the image with which it is easy to recognize the condition of a blotch, and the image with which it is easy to recognize pores and texture of face skin.

Note that such an electronic mirror may have a configuration where two imaging apparatuses A and an autostereoscopic display.

FIG. 33(b) is a front view of a stereoscopic electronic mirror AP6. The stereoscopic electronic mirror AP6 includes a frame T2, the frame T2 including therein an autostereoscopic display J2, two imaging apparatuses A1 and A2, the polarized illumination Qa and the non-polarized illumination Qb. The autostereoscopic display may be a parallax barrier-type autostereoscopic display or a lenticular-type autostereoscopic display.

The face of a person, who is the object, is irradiated with light from the polarized illumination Qa and light from the non-polarized illumination Qb, and the two imaging apparatuses A1 and A2 can therefore simultaneously obtain both image information having polarization information of a person, who is the object, and normal image information. The image information obtained by the two imaging apparatuses A are displayed in real time on the autostereoscopic display J2 wherein the image information are images with parallax being inverted left and right.

By using such an electronic mirror AP6, it is possible to check the mirror image of the user himself/herself in a more realistic manner than with the electronic mirror AP4.

Embodiment 15 may have a configuration where any of the imaging apparatuses A described in Embodiments 1 and 3 to 12 is combined with the imaging system AP1 described in Embodiment 2.

Where the display J1 and the stereoscopic display J2 are formed by a liquid crystal display, the object is irradiated also with light from the liquid crystal display itself, and therefore the polarization axis of the polarization filter on the front surface side of the liquid crystal display may be the same as the polarization axis of the polarized illumination Qa. Then, the polarization direction of light from the liquid crystal display which irradiates the object can be made equal to the polarization direction of light from the polarized illumination.

While the configuration includes the polarized illumination and non-polarized illumination in the present embodiment, it may include only the polarized illumination.

Where the configuration includes only the polarized illumination, the configuration may include two polarized illuminations whose transmission polarization axes are orthogonal to each other.

The light source for a polarized illumination may be formed only by a white light source, or may be a polarized illumination having a configuration where a blue light source is added to a white light source or a configuration where a green light source is added to a white light source in order to compensate for the attenuation of light through polarization filters in optical regions of the imaging apparatus.

Other Embodiments

While Embodiments 1 to 10 and 12 are directed to a configuration where the signal processing section C is provided, the signal processing section C may be absent. In such a case, the process to be performed by the signal processing section C may be performed by using a personal computer, or the like, external to the imaging apparatus. That is, the present invention may be realized by a system including an imaging apparatus and an external signal processing device, wherein the imaging apparatus includes the lens optical system L, the arrayed optical device K and the imaging device N.

Figure 34:
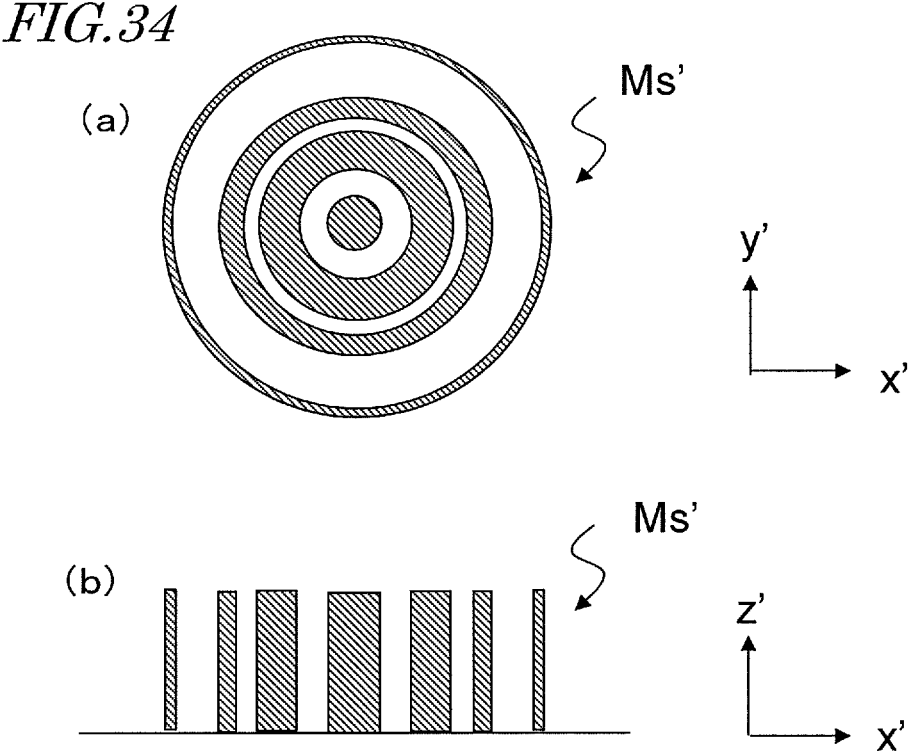
FIGS. 34(a) and 34(b) are a plan view and a cross-sectional view showing a diffraction optical device which can be provided on an imaging device.

While a microlens provided on each pixel of the imaging device has a lens surface having a curved surface shape in Embodiments 1 to 15, a microlens of a different shape may be provided on the imaging device. For example, one may use a diffraction optical device for condensing light by virtue of a distribution of materials having different refractive indices as disclosed in Japanese Laid-Open Patent Publication No. 2008-10773. FIGS. 34(a) and 34(b) are a plan view and a cross-sectional view showing an example of a diffraction optical device Ms'. In FIGS. 34(a) and 34(b), optical member portions indicated by hatching and the surrounding portions are formed by materials or media having different refractive indices from each other. As shown in FIGS. 34(a) and 34(b), the diffraction optical device Ms' includes, for example, a plurality of cylindrical optical members arranged in a concentric pattern, each of which has a ring shape on a plane parallel to the plane on which pixels are formed and which extend in a direction perpendicular to the plane. It is possible to adjust the refractive index of the diffraction optical device Ms' based on the refractive index difference between optical members and surrounding portions, the size of the cylinder, the interval between cylinders arranged in a concentric pattern, etc. The shape of the optical member is not limited to cylindrical, but may be rotationally asymmetric with respect to the optical axis. While FIGS. 34(a) and 34(b) are directed to a binary diffraction optical device having two levels, it may be a multi-level diffraction optical device having three or more levels.

The diffraction optical device Ms' having such a configuration can be manufactured by using semiconductor photolithography, for example. Microlenses having a conventional lens surface are manufactured by thermally deforming a resin, for example, and it was therefore difficult to vary the curved surface of the lens surface between a plurality of microlenses provided on a plurality of pixels of the imaging device. In contrast, when the diffraction optical device Ms' is used, the optical characteristics can be changed by varying the dimensions of the optical members between a plurality of pixels of the imaging device. Therefore, with the optical system L and the arrayed optical device K, it is possible to efficiently condense light onto pixels even if light beams are incident slantly onto pixels of the imaging device N.

By increasing the refractive index difference of the diffraction optical device Ms', it is possible to shorten the focal length of the diffraction optical device Ms'. Therefore, as described in Embodiment 10, for example, where the arrayed optical device K is provided on the imaging surface Ni of the imaging device, it is possible to decrease the combined thickness of the arrayed optical device K and the diffraction optical device Ms', and it is therefore possible to decrease the height of the imaging device. Thus, it is possible to realize an imaging apparatus having a small thickness.

One may also employ a configuration where the area of each optical region is limited by the stop S, and a configuration where the optical devices L1s and L1p are arranged on the same plane. For example, as shown in FIG. 35(a), the first optical region D1 primarily passes therethrough light oscillating in the direction of the first polarization axis, the second optical region D2 passes therethrough light oscillating in any direction and passes therethrough light of the wavelength band of near-infrared light, the third optical region D3 passes therethrough light oscillating in any direction in the visible light band, and the fourth optical region D4 passes therethrough light oscillating in any direction in the visible light band, wherein the area of the fourth optical region is smaller than the area of the third optical region D3. Such a configuration is advantageous for imaging apparatuses of on-vehicle applications. With such a configuration, light having passed through the first optical region D1 makes it easier to detect a lane of a wet road as shown in Embodiment 1. By using a headlight of near-infrared light while driving at night, light having passed through the second optical region D2 makes it easier to detect a person, an obstacle and road conditions that are difficult to detect with human eyes. Since the image of light having passed through the third optical region D3 and the image of light having passed through the fourth optical region D4 are images having different amounts of exposure from each other, it is possible to generate an image with a wide dynamic range by synthesizing these images together. With an image having a wide dynamic range, it is possible, near the exit of a tunnel, to obtain an image showing the inside and the outside of the tunnel, with little blown out highlights or blocked up shadows. With such a configuration, it is possible to detect circumstances in front under any environment using a single imaging apparatus. With such a configuration, it is possible to generate an image with a wide dynamic range by setting the area of the third optical region D3 and the area of the fourth optical region D4 to be equal to each other, and inserting an ND filter in the fourth region.

One may also employ a configuration where the amount of light passing through the fourth optical region D4 and the amount of light passing through the third optical region D3 are equal to each other as shown in FIG. 35(b). With such a configuration, an image obtained by adding together an image of light having passed through the third optical region D3 and an image of light having passed through the fourth optical region D4 is different, in terms of the amount of exposure, from an image of light having passed through the first optical region D1. Therefore, it is possible to generate an image with a wide dynamic range by combining these images together.

One may also employ a configuration where the area of the first optical region D1 is made smaller as shown in FIG. 35(c) so as to increase the exposure ratio from that of the configuration of FIG. 35(b).

Note that the optical regions D3 and D4 of FIGS. 35(a), 35(b) and 35(c) may be a transparent glass or may be hollow.

One may also employ a configuration where the second optical region is the same as the third and fourth optical regions as shown in FIG. 35(d). One may also employ a configuration where the area of the first optical region D1 is reduced as compared with FIG. 35(d).

INDUSTRIAL APPLICABILITY

The imaging apparatus disclosed in the present application is useful as an imaging apparatus of a digital still camera, a digital video camera, an vehicle camera, a surveillance camera, a skin diagnosis camera, an endoscopic camera, etc. It can also be applied to an imaging system such as a microscope or an electronic mirror.

REFERENCE SIGNS LIST

A Imaging apparatus
L Lens optical system
L1s, L1p Optical device
L2 Lens
D1, D2, D3, D4 Optical region S Stop
K Arrayed optical device
N Imaging device
Ni Imaging surface
M1, M2, Md Optical element in arrayed optical device
Ms Microlens on imaging device
P1 to P4 Pixels on imaging device
C Signal processing section

The invention claimed is:

1. An imaging apparatus comprising:
a lens optical system;
an imaging device including a plurality of first pixels and a plurality of second pixels on which light having passed through the lens optical system is incident; and
an arrayed optical device being arranged between the lens optical system and the imaging device and including a plurality of optical elements each having a lens surface, wherein:
the lens optical system includes:
a plurality of optical regions, and the plurality of optical regions include a first optical region including a polarizing filter which primarily passes therethrough light oscillating in a direction of a first polarization axis and a second optical region which does not include a polarizing filter and passes therethrough light oscillating in any direction; and
a stop including a region through which light of all field angles, that passes through the plurality of optical regions, passes, wherein the plurality of optical regions are arranged in the vicinity of the stop; and
the plurality of optical elements of the arrayed optical device make light having passed through the first optical region incident on the plurality of first pixels and light having passed through the second optical region incident on the plurality of second pixels.

2. The imaging apparatus of claim 1, wherein the first optical region passes therethrough light of a first wavelength band, and the second optical region passes therethrough light of a second wavelength band.

3. The imaging apparatus of claim 2, wherein the first wavelength band is a wavelength band of near infrared light.

4. The imaging apparatus of claim 1 wherein:
the plurality of optical regions of the lens optical system further includes a third optical region other than the first and second optical regions;
the third optical region primarily passes therethrough light oscillating in a direction of a second polarization axis which is different from the first polarization axis; and
the arrayed optical device makes light having passed through the third optical region incident on a plurality of third pixels other than the plurality of first and second pixels.

5. The imaging apparatus of claim 1 wherein:
the plurality of optical regions of the lens optical system further include third and fourth optical regions other than the first and second optical regions;
the first, second, third and fourth optical regions pass therethrough light of first, second, third and fourth wavelength bands which are different from one another; and
the arrayed optical device makes light having passed through the third and fourth optical regions incident on a plurality of third and fourth pixels, respectively, other than the plurality of first and second pixels.

6. The imaging apparatus of claim 5 wherein the arrayed optical device is a microlens array.

7. The imaging apparatus of claim 6, wherein each of the plurality of optical elements is arranged so as to correspond to one of the plurality of first pixels, one of the plurality of second pixels, one of the plurality of third pixels, and one of the plurality of fourth pixels.

8. The imaging apparatus of claim 1 wherein:
the plurality of optical regions of the lens optical system further include third and fourth optical regions other than the first and second optical regions;
the first and third optical regions pass therethrough light of the same wavelength band, and second and fourth optical regions pass therethrough light of wavelength bands different from wavelength bands of light passing through the first and the third optical regions, respectively; and
the arrayed optical device makes light having passed through the third and fourth optical regions incident on a plurality of third and fourth pixels, respectively, other than the plurality of first and second pixels.

9. The imaging apparatus of claim 8, wherein the third optical region primarily passes therethrough light oscillating in a direction of a second polarization axis different from the first polarization axis.

10. The imaging apparatus of claim 1, wherein:
the imaging device further includes a plurality of third and fourth pixels on which light having passed through the lens optical system is incident;
the plurality of optical regions further include third and fourth optical regions;
the third optical region passes therethrough light oscillating in any direction;
the arrayed optical device makes light having passed through the third and fourth optical regions incident on the plurality of third and fourth pixels; and
the plurality of first, second and third pixels include filters having first, second and third spectral transmittance characteristics, respectively.

11. The imaging apparatus of claim 10, wherein:
the plurality of fourth pixels have the first spectral transmittance characteristics; and
the fourth optical region passes therethrough light of a predetermined wavelength band and passes therethrough light oscillating in a direction of a second polarization axis different from the first polarization axis.

12. The imaging apparatus of claim 11, wherein the first, second, third and fourth pixels of the imaging device are arranged in a Bayer array.

13. The imaging apparatus of claim 1 wherein:
the plurality of first pixels include 1A and 1B pixels, the plurality of second pixels include 2A and 2B pixels, the plurality of third pixels include 3A and 3B pixels, and the plurality of fourth pixels include 4A and 4B pixels;
an optical element in the $k^{th}$ row makes light having passed through the first region incident on the 1A pixel and the 3A pixel and makes light having passed through the second region incident on the 2B pixel and the 4B pixel; and
an optical element in the $k+1^{th}$ row makes light having passed through the first region incident on a plurality of 2A pixels and the 4A pixel and makes light having passed through the second region incident on the 1B pixel and the 3B pixel.

14. The imaging apparatus of claim 1 wherein the arrayed optical device is a lenticular lens.

15. The imaging apparatus of claim 14, wherein:
- in the arrayed optical device, the lens surfaces of the plurality of optical elements are each a cylindrical surface extending in a first direction, and the plurality of optical elements are arranged in a second direction; and
- each of the plurality of optical elements is arranged so as to correspond to two rows of pixels including one row of first pixels and one row of second pixels.

16. The imaging apparatus of claim 1, wherein the arrayed optical device is formed on the imaging device.

17. The imaging apparatus of claim 16, further comprising a microlens provided between the arrayed optical device and the imaging device,
- wherein the arrayed optical device is formed on the imaging device with the microlens interposed therebetween.

18. The imaging apparatus of claim 17, wherein the microlens provided between the arrayed optical device and the imaging device is a binary refractive index distribution type optical element or a multi-level refractive index distribution type optical element.

19. The imaging apparatus of claim 1, wherein each optical element of the plurality optical elements is configured to selectively determine the outgoing direction of an incoming light ray according to an angle of incidence of the incoming light ray.

* * * * *